(12) United States Patent
Maroncelli et al.

(10) Patent No.: US 12,171,662 B1
(45) Date of Patent: Dec. 24, 2024

(54) HEART CHAMBER RESHAPING AND VALVE REPAIR SYSTEM

(71) Applicant: Approxima Srl, Seregno (IT)

(72) Inventors: Edoardo Maroncelli, Milan (IT);
Michal Lukasz Jaworek, Milan (IT);
Fabio Pappalardo, Seregno (IT);
Giulia Pisoni, Seregno (IT)

(73) Assignee: Approxima Srl, Seregno (IT)

( * ) Notice: Subject to any disclaimer, the term of this patent is extended or adjusted under 35 U.S.C. 154(b) by 0 days.

(21) Appl. No.: 18/495,596

(22) Filed: Oct. 26, 2023

(51) Int. Cl.
*A61F 2/24* (2006.01)

(52) U.S. Cl.
CPC .................................. *A61F 2/2478* (2013.01)

(58) Field of Classification Search
CPC ................. A61F 2/2478; A61F 2/2487; A61F 2220/0075; A61F 2250/0007
See application file for complete search history.

(56) References Cited

U.S. PATENT DOCUMENTS

| | | | |
|---|---|---|---|
| 6,537,198 B1 | 3/2003 | Vidlund et al. | |
| 7,431,692 B2 | 10/2008 | Zollinger | |
| 8,147,542 B2 | 4/2012 | Maisano et al. | |
| 9,597,184 B2 | 3/2017 | Machold et al. | |
| 11,116,497 B2 | 9/2021 | Maisano et al. | |
| 2003/0078465 A1 | 4/2003 | Pai et al. | |
| 2005/0075723 A1 | 4/2005 | Schroeder | |
| 2005/0197692 A1 | 9/2005 | Pai et al. | |
| 2005/0222488 A1 | 10/2005 | Chang et al. | |
| 2006/0015003 A1 | 1/2006 | Moaddes et al. | |
| 2006/0149123 A1 | 7/2006 | Vidlund et al. | |
| 2007/0073370 A1 | 3/2007 | Zielinski et al. | |
| 2007/0112425 A1 | 5/2007 | Schaller | |

(Continued)

FOREIGN PATENT DOCUMENTS

| | | |
|---|---|---|
| CA | 2837206 A1 | 12/2012 |
| CA | 2837206 C | 12/2012 |

(Continued)

OTHER PUBLICATIONS

International Search Report and Written Opinion issued in PCT/IB2021/054150, mailed Sep. 2, 2021.

*Primary Examiner* — Carrie R Dorna
(74) *Attorney, Agent, or Firm* — Nelson Mullins Riley & Scarborough LLP

(57) ABSTRACT

An implantable assembly adapted for reshaping a cardiac chamber of a heart in a patient is disclosed. The assembly is implanted by a tool having a tool proximal portion and a distal portion. The assembly includes an active anchor including an abutment portion adapted to abut against a wall of the chamber of the heart and a tether portion rotatably coupled to the abutment portion. Each of the abutment portion and the tether portion configured to independently couple with a tool. The assembly further includes an interventricular septal anchor for coupling to a septum of the heart and a tether having a working portion having a first length, extending between the active anchor and the septal anchor, and a tether proximal portion having a second length. The abutment portion is releasably locked to the tether portion and configured such that a preselected torque applied to the tether portion of the active anchor unlocks and causes a relative rotation of the tether portion with respect to the abutment portion.

12 Claims, 32 Drawing Sheets

(56) References Cited

U.S. PATENT DOCUMENTS

| | | |
|---|---|---|
| 2007/0203391 A1 | 8/2007 | Bloom et al. |
| 2008/0086164 A1 | 4/2008 | Rowe |
| 2008/0195126 A1 | 8/2008 | Solem |
| 2010/0023117 A1 | 1/2010 | Yoganathan et al. |
| 2010/0094314 A1* | 4/2010 | Hernlund ............ A61B 17/0487 606/232 |
| 2010/0185278 A1 | 7/2010 | Schankereli |
| 2011/0029071 A1 | 2/2011 | Zlotnick et al. |
| 2011/0106245 A1* | 5/2011 | Miller .................. A61F 2/2442 623/2.11 |
| 2011/0178362 A1 | 7/2011 | Evans et al. |
| 2012/0191169 A1 | 7/2012 | Rothstein et al. |
| 2013/0030522 A1 | 1/2013 | Rowe et al. |
| 2013/0090672 A1* | 4/2013 | Butler .................. A61B 5/0215 606/151 |
| 2014/0379006 A1 | 12/2014 | Sutherland et al. |
| 2016/0038130 A1 | 2/2016 | Schaller et al. |
| 2016/0174964 A1 | 6/2016 | Tobis |
| 2016/0262741 A1 | 9/2016 | Gilmore et al. |
| 2017/0086975 A1 | 3/2017 | Gilmore et al. |
| 2017/0340329 A1 | 11/2017 | Groothuis et al. |
| 2018/0103947 A1 | 4/2018 | Nobles et al. |
| 2018/0344311 A1 | 12/2018 | Gilmore et al. |
| 2019/0133575 A1 | 5/2019 | Maisano et al. |
| 2019/0167428 A1 | 6/2019 | Tobis |
| 2019/0274833 A1 | 9/2019 | Van Bladel et al. |
| 2019/0343626 A1 | 11/2019 | Smirnov et al. |
| 2019/0343633 A1 | 11/2019 | Garvin et al. |
| 2019/0343634 A1 | 11/2019 | Garvin et al. |
| 2019/0350709 A1 | 11/2019 | Maisano et al. |
| 2019/0365539 A1 | 12/2019 | Rabito et al. |
| 2019/0380699 A1 | 12/2019 | Bak-Boychuk et al. |
| 2020/0113685 A1 | 4/2020 | Miller et al. |
| 2022/0054270 A1 | 2/2022 | Manash |

FOREIGN PATENT DOCUMENTS

| | | |
|---|---|---|
| CN | 111772874 A | 10/2020 |
| CN | 109044565 B | 3/2021 |
| CN | 214549745 U | 11/2021 |
| CN | 214804938 U | 11/2021 |
| DE | 102006028964 A1 | 12/2007 |
| EP | 1039851 A1 | 10/2000 |
| EP | 1367962 A2 | 12/2003 |
| EP | 1039851 B1 | 7/2005 |
| EP | 1628599 A2 | 3/2006 |
| EP | 1788983 A2 | 5/2007 |
| EP | 1959866 A1 | 8/2008 |
| EP | 1986735 A2 | 11/2008 |
| EP | 2081519 A2 | 7/2009 |
| EP | 2525741 A1 | 11/2012 |
| EP | 2081519 B1 | 4/2014 |
| EP | 2750631 A1 | 7/2014 |
| EP | 2814427 A1 | 12/2014 |
| EP | 2863844 A1 | 4/2015 |
| EP | 2961351 A1 | 1/2016 |
| EP | 2999435 A1 | 3/2016 |
| EP | 3013250 A1 | 5/2016 |
| EP | 3060175 A1 | 8/2016 |
| EP | 3120811 A2 | 1/2017 |
| EP | 3120811 A3 | 1/2017 |
| EP | 3242629 A1 | 11/2017 |
| EP | 3270794 A1 | 1/2018 |
| EP | 3337428 A1 | 6/2018 |
| EP | 3360515 A1 | 8/2018 |
| EP | 3386440 A1 | 10/2018 |
| EP | 3558169 A1 | 10/2018 |
| EP | 2961351 B1 | 11/2018 |
| EP | 3624705 A1 | 11/2018 |
| EP | 2814427 B1 | 12/2018 |
| EP | 3242629 B1 | 12/2018 |
| EP | 2575685 B1 | 2/2019 |
| EP | 1959866 B1 | 3/2019 |
| EP | 3468506 A1 | 4/2019 |
| EP | 3538028 A1 | 9/2019 |
| EP | 3579761 A2 | 12/2019 |
| EP | 3595587 A1 | 1/2020 |
| EP | 3600143 A1 | 2/2020 |
| EP | 3630014 A1 | 4/2020 |
| EP | 3682852 A1 | 7/2020 |
| EP | 3689258 A1 | 8/2020 |
| EP | 3697346 A1 | 8/2020 |
| EP | 3713518 A1 | 9/2020 |
| EP | 3538028 B1 | 12/2020 |
| EP | 3843664 A1 | 7/2021 |
| EP | 3624705 B1 | 12/2021 |
| EP | 2400922 A1 | 1/2022 |
| EP | 2400922 B1 | 1/2022 |
| EP | 3558169 B1 | 1/2022 |
| EP | 3697346 B1 | 1/2022 |
| EP | 2750631 B1 | 11/2022 |
| EP | 2999435 B1 | 12/2022 |
| WO | 1999030647 A | 6/1999 |
| WO | 2001070116 A1 | 9/2001 |
| WO | 2002030292 A1 | 4/2002 |
| WO | 2009026145 A1 | 2/2009 |
| WO | 2009046343 A1 | 4/2009 |
| WO | 2009081396 A2 | 7/2009 |
| WO | 2009081396 A3 | 7/2009 |
| WO | 2011154942 A2 | 12/2011 |
| WO | 2013049766 A1 | 4/2013 |
| WO | 2013096757 A1 | 6/2013 |
| WO | 2013123388 A1 | 8/2013 |
| WO | 2014141239 A1 | 9/2014 |
| WO | 2014164028 A1 | 10/2014 |
| WO | 2015063580 A2 | 5/2015 |
| WO | 2015063580 A3 | 5/2015 |
| WO | 2015109243 A1 | 7/2015 |
| WO | 2015112971 A1 | 7/2015 |
| WO | WO 2015/138306 * 9/2015 ............ A61F 2/2478 |
| WO | WO-2015138306 A2 * 9/2015 ............ A61B 90/06 |
| WO | 2015151627 A1 | 10/2015 |
| WO | 2015193728 A2 | 12/2015 |
| WO | 2015193728 A3 | 12/2015 |
| WO | 2015193728 A8 | 12/2015 |
| WO | 2016110735 A1 | 7/2016 |
| WO | 2016154498 A1 | 9/2016 |
| WO | 2017087688 A1 | 5/2017 |
| WO | 2017103843 A1 | 6/2017 |
| WO | 2017205358 A1 | 11/2017 |
| WO | 2018145249 A1 | 8/2018 |
| WO | 2018148324 A1 | 8/2018 |
| WO | 2018148364 A2 | 8/2018 |
| WO | 2018148364 A3 | 8/2018 |
| WO | 2018160456 A1 | 9/2018 |
| WO | 20181699878 A1 | 9/2018 |
| WO | 2018183632 A1 | 10/2018 |
| WO | 2018204518 A1 | 11/2018 |
| WO | 2019006152 A1 | 1/2019 |
| WO | 2019173385 A1 | 9/2019 |
| WO | 2019217638 A1 | 11/2019 |
| WO | 2019217638 A9 | 11/2019 |
| WO | 2019231744 A1 | 12/2019 |
| WO | 2020032925 A1 | 2/2020 |
| WO | 2020096861 A1 | 5/2020 |
| WO | 2020150497 A1 | 7/2020 |
| WO | 2020167456 A1 | 8/2020 |
| WO | 2020176201 A1 | 9/2020 |
| WO | 2020227556 A1 | 11/2020 |
| WO | 2020231237 A2 | 11/2020 |
| WO | 2020231237 A3 | 11/2020 |
| WO | 2020236417 A1 | 11/2020 |
| WO | 2021024183 A1 | 2/2021 |
| WO | 2021150913 A1 | 7/2021 |
| WO | WO 2021/240289 * 12/2021 ............ A61F 2/2487 |
| WO | WO-2021240289 A1 * 12/2021 ............ A61F 2/2487 |

* cited by examiner

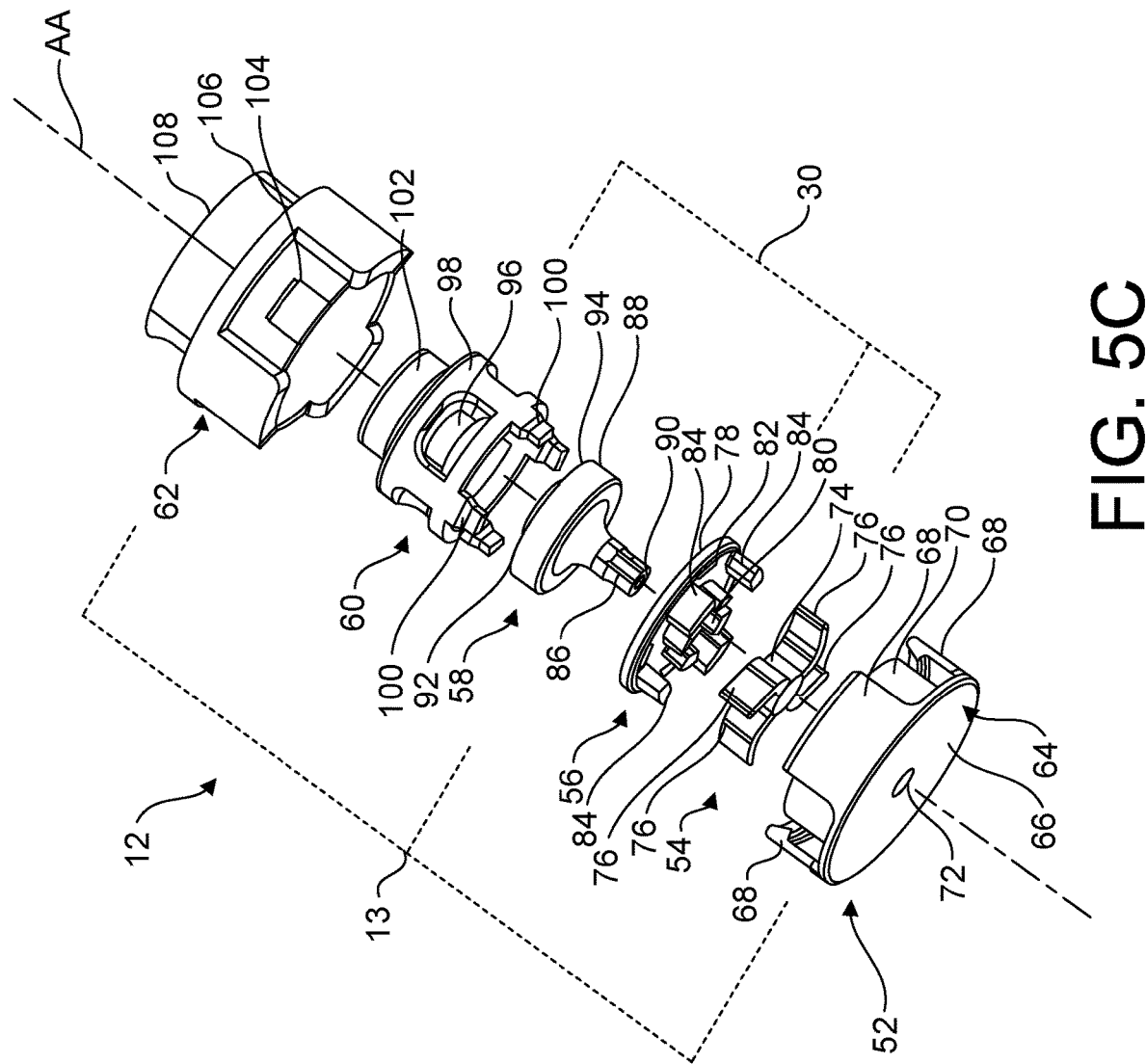

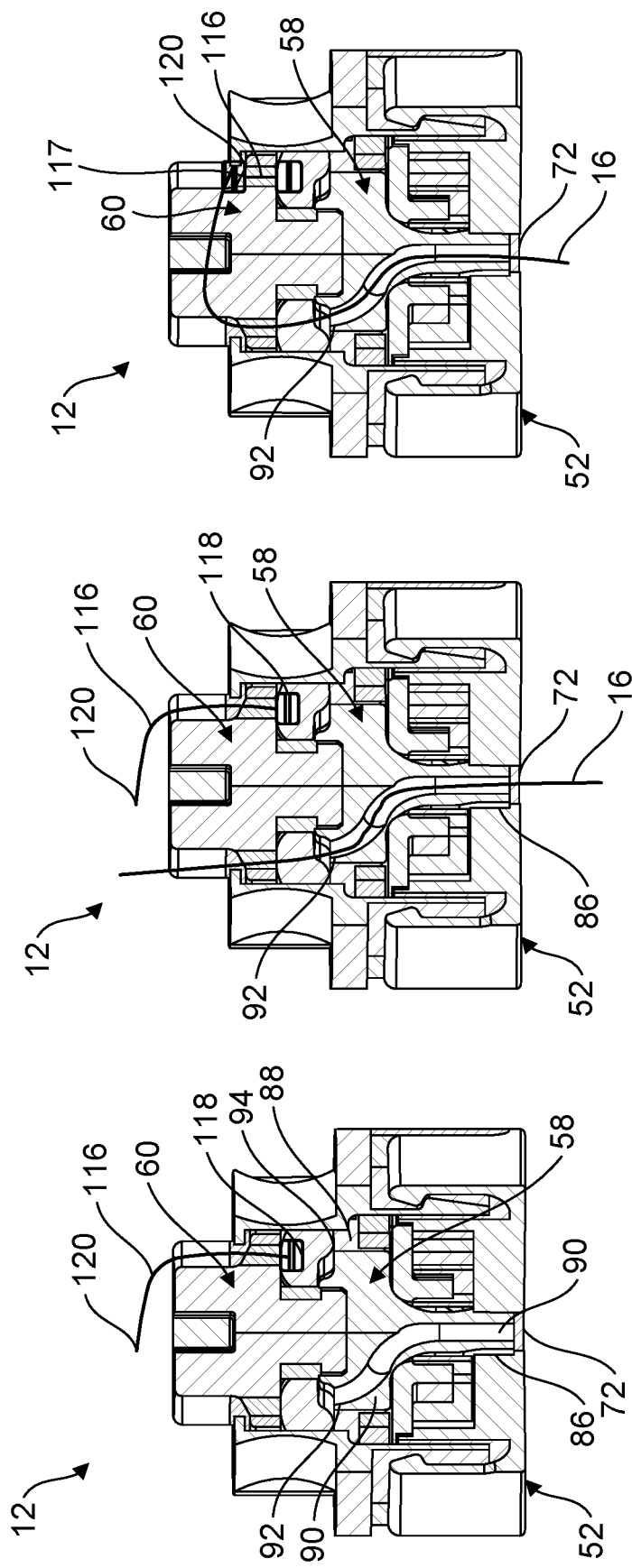

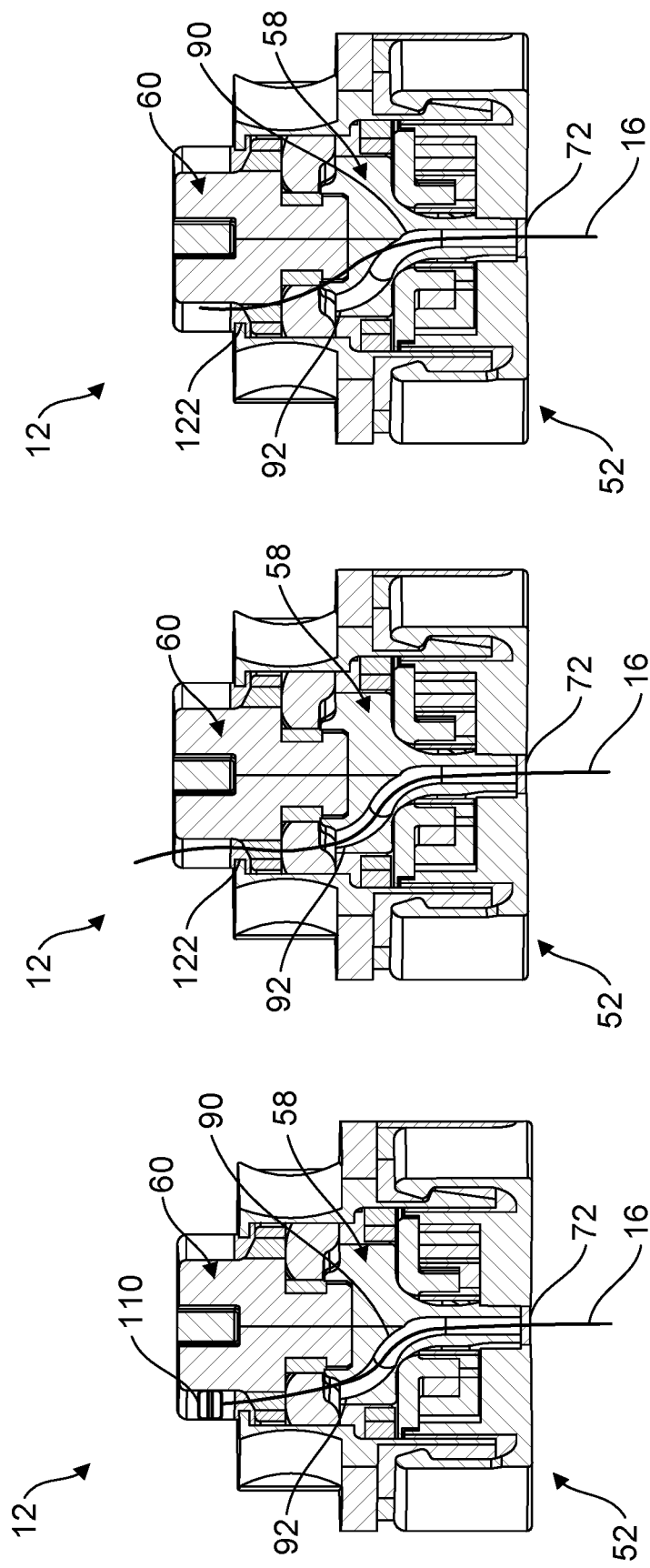

HEART CHAMBER RESHAPING AND VALVE REPAIR SYSTEM

TECHNICAL FIELD

The present disclosure relates to medical systems for the heart. More specifically, the present disclosure relates to a heart chamber reshaping and valve repair systems and methods for modifying the distance between native heart structures.

BACKGROUND

A native atrioventricular heart valve can become damaged and unable to close effectively. For instance, a characteristic type of damage relates to the structural alteration of the ventricle as dilated. The muscular-fibrous ring forming the passage opening can also become dilated. These alterations cause the inability of the valve leaflets to arrange themselves in the coaptation position and can cause an undesirable regurgitation flow from the ventricle towards the atrium, which can limit the effectiveness of the heart pump.

In a typical procedure to repair an atrioventricular heart valve, such as the mitral valve, a hoop ring is implanted to reinforce the annulus and to return the annulus to near the original shape, which can allow the leaflets to be brought closer together with the valve closed. In a proposed procedure, a clip can be inserted via a catheter to capture and bring the free edge of the valve leaflets closer together to form a double orifice valve. Another approach includes the implantation of devices for bringing the walls of the heart chambers (atria and ventricles) closer together or bringing the papillary muscles forming the anchoring structures of the tendon to the inner side of the ventricle closer together.

SUMMARY

The invention, according to Example 1 is an assembly adapted to be implanted by a tool, the assembly adapted for reshaping a cardiac chamber of a heart in a patient. The assembly includes an active anchor including an abutment portion adapted to abut against a wall of a ventricle of the heart and a tether portion rotatably coupled to the abutment portion, each of the abutment portion and the tether portion configured to independently couple with the tool. It further includes an interventricular septal anchor for coupling to a septum of the heart and a tether having a working portion having a first length, extending between the active anchor and the septal anchor, and a tether proximal portion having a second length. The abutment portion is releasably coupled to the tether portion and configured such that a predetermined torque applied to the tether portion unlocks and causes a relative rotation of the tether portion with respect to the abutment portion, which rotation adjusts the first length of the working portion and the second length of the tether proximal portion.

In Example 2, the assembly of Example 1 further comprises a tool having a tool proximal portion and a tool distal portion, wherein the tool proximal portion includes an interface and the tool distal portion includes a hollow shaft and an adjustment component adapted to engage the tether portion of the active anchor.

Example 3 is the assembly of Example 2 wherein the tool proximal portion includes an interface operatively coupled to the adjustment component, the interface adapted to allow a user to impart relative rotation to the adjustment component.

Example 4 is the assembly of any of Examples 1 to 3 wherein a distal end of the hollow shaft includes an engagement member configured to engage the abutment portion of the active anchor so as to resist rotation thereof.

Example 5 is the assembly of any of Examples 1 to 4 wherein the engagement member includes one or more fingers extending from the distal end of the hollow shaft.

Example 6 is the assembly of any of Examples 1 to 5 wherein the active anchor is configured to allow the relative rotation of the tether portion with respect to the abutment portion to occur in both directions.

Example 7 is the assembly of Example 6 wherein the tether portion of the active anchor includes a winding shaft configured such that the relative rotation of the tether portion with respect to the abutment portion in a first direction causes the tether proximal portion to wind around the winding shaft and the relative rotation of the tether portion with respect to the abutment portion in an opposite direction causes the tether to unwind from the shaft.

Example 8 is the assembly of any of Examples 1 to 7 wherein the active anchor further comprises a lock mechanism for resisting the relative rotation of the tether portion with respect to the abutment portion.

Example 9 is a system adapted for reshaping a cardiac chamber of a heart in a patient. The system includes a tool including a hollow shaft disposed about an adjustment component, an active anchor including an abutment portion adapted to abut against a wall of the ventricle of the heart and a tether portion coupled to the abutment portion, the tether portion configured to couple with the adjustment component of the tool, an interventricular septal anchor for coupling to a septum of the heart and a tether having a working portion having a first length, extending between the active anchor and the septal anchor, and a tether proximal portion having a second length. The adjustment component of the tool is adapted to impart a force on the active anchor so as to cause a relative rotation of the tether portion with respect to the abutment portion, which rotation adjusts the first length of the working portion and the second length of the tether proximal portion. The tether portion of the active anchor includes a coupling mechanism adapted to couple with an end of the tether.

Example 10 is the system of Example 9 wherein the active anchor further comprises a lock mechanism for resisting the relative rotation of the tether portion with respect to the abutment portion.

Example 11 is the system of Example 10 wherein the active anchor is configured such that a predetermined torque applied to the tether portion of the active anchor overcomes the lock mechanism and allows the relative rotation of the tether portion with respect to the abutment portion.

Example 12 is the system of any of Examples 9 to 11 wherein the active anchor is configured to allow the relative rotation of the tether portion with respect to the abutment portion to occur in both directions.

Example 13 is the system of any of Examples 9 to 12 wherein the coupling mechanism is a support tether coupled to the tether portion of the active anchor.

Example 14 is the system of any of Examples 9 to 13 wherein the coupling mechanism is an adjustable clamping mechanism having an open configuration and a lock configuration for securing to an end of the tether.

Example 15 is a system adapted for reshaping a cardiac chamber of a heart in a patient. The system includes a tool including a hollow shaft disposed about an adjustment component, an active anchor including an abutment portion adapted to abut against a wall of the ventricle of the heart and a tether portion coupled to the abutment portion, the tether portion configured to couple with the adjustment component of the tool, an interventricular septal anchor for coupling to a septum of the heart and a tether having a working portion having a first length, extending between the active anchor and the septal anchor, and a tether proximal portion having a second length. The adjustment component of the tool is adapted to impart a torque on the active anchor so as to cause a relative rotation of the tether portion with respect to the abutment portion, which rotation adjusts the first length of the working portion and the second length of the tether proximal portion. The engagement member of the tool is adapted to transition between a coupling configuration wherein the engagement member is coupled to the active anchor and a decoupling configuration wherein the engagement member is decoupled from the active anchor.

Example 16 is the system of Example 15 wherein the tool further comprising a security mechanism adapted to prevent the engagement member from transitioning from the coupling to the decoupling configuration.

Example 17 is a system adapted for reshaping a cardiac chamber of a heart in a patient. The system includes a tool including a hollow shaft disposed about an adjustment component, the tool including an adjustment interface having a first position to allow rotation of the adjustment component in a first direction and a second position to allow rotation of the adjustment component in a second direction, an active anchor including an abutment portion adapted to abut against a wall of the ventricle of the heart and a tether portion coupled to the abutment portion, the tether portion configured to couple with the adjustment component of the tool, an interventricular septal anchor for coupling to a septum of the heart and a tether having a working portion having a first length, extending between the active anchor and the septal anchor, and a tether proximal portion having a second length. The adjustment component of the tool is adapted to impart a torque on the active anchor so as to cause a relative rotation of the tether portion with respect to the abutment portion, which rotation adjusts the first length of the working portion and the second length of the tether proximal portion.

Example 18 is the system of Example 17 wherein the adjustment interface further has a third position to allow rotation of the adjustment component in both directions.

Example 19 is the system of either of Examples 17 or 18 wherein the adjustment interface of the tool includes a graduated scale adapted to visually indicate a position of the adjustment component.

Example 20 is the system of any of Examples 17 to 19 wherein the active anchor further comprises a lock mechanism for resisting the relative rotation of the tether portion with respect to the abutment portion.

Example 21 is a method of reshaping a cardiac chamber of a heart of a patient. The method includes attaching an interventricular septal anchor of an assembly to a septum of the heart, abutting an abutment portion of an active anchor of the assembly against a wall of a ventricle of the heart, the active anchor further comprising a tether portion rotatably coupled to the abutment portion, coupling a tether to the active anchor and the septal anchor, the tether having a working portion having a first length, extending between the active anchor and the septal anchor, and a tether proximal portion having a second length and tensioning the tether with a preselected torque applied to the tether portion to cause a relative rotation of the tether portion with respect to the abutment portion, which rotation adjusts the first length of the working portion and the second length of the tether proximal portion.

Example 22 is the method of Example 21 wherein at least one of the septal anchor and the active anchor are delivered via the patient's vasculature.

Example 23 is the method of Example 22 wherein at least a portion of the interventricular septal anchor is delivered via the patient's vasculature and the active anchor is delivered from outside of the heart.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5C is an exploded view of the example active anchor of FIG. 5A from a first perspective.

FIGS. 6A-6F are side sectioned views illustrating example methods of attaching a tether to the example active anchor of FIG. 5A.

Figure 2:
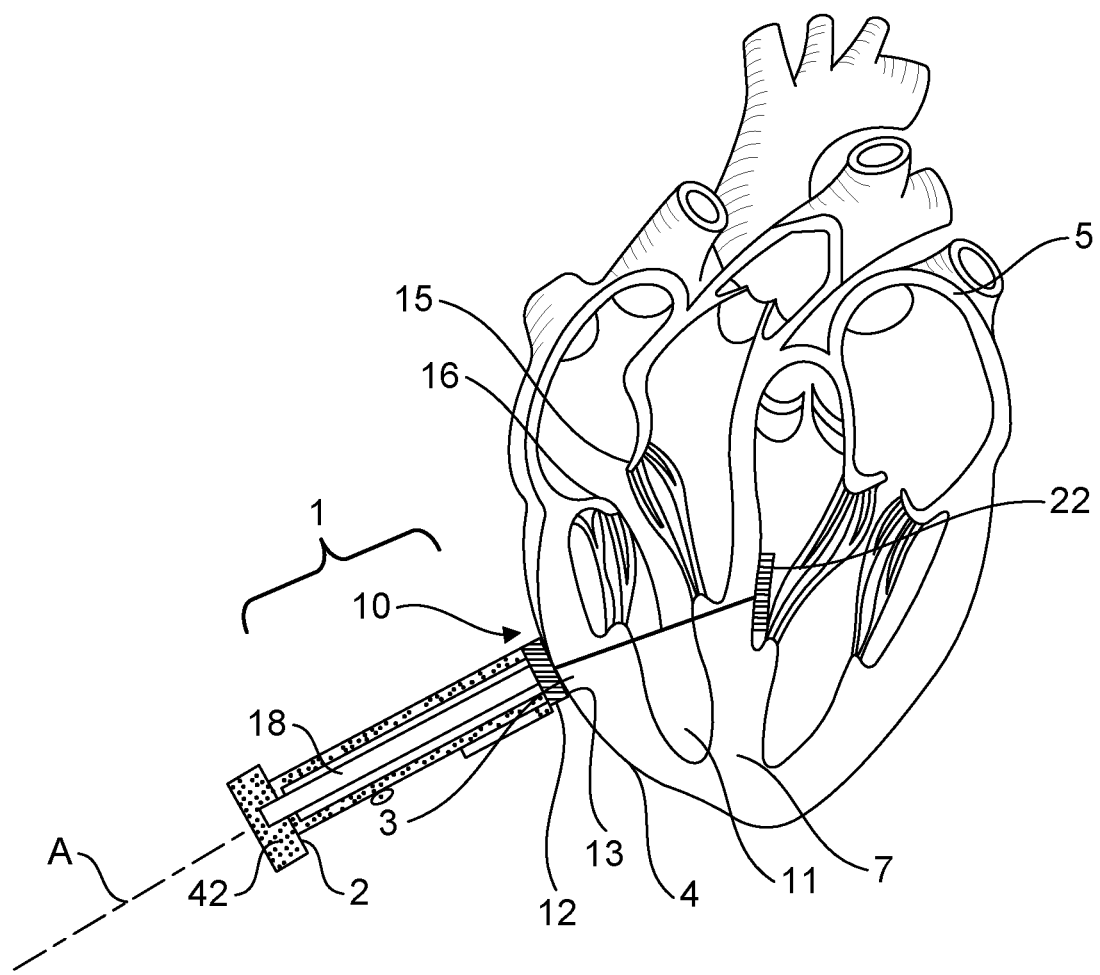
FIG. 2 is a schematic diagram illustrating the example valve repair assembly implanted in the heart of FIG. 1 in combination with an example tool to form an example valve repair system of the present disclosure.
Figure 9A:
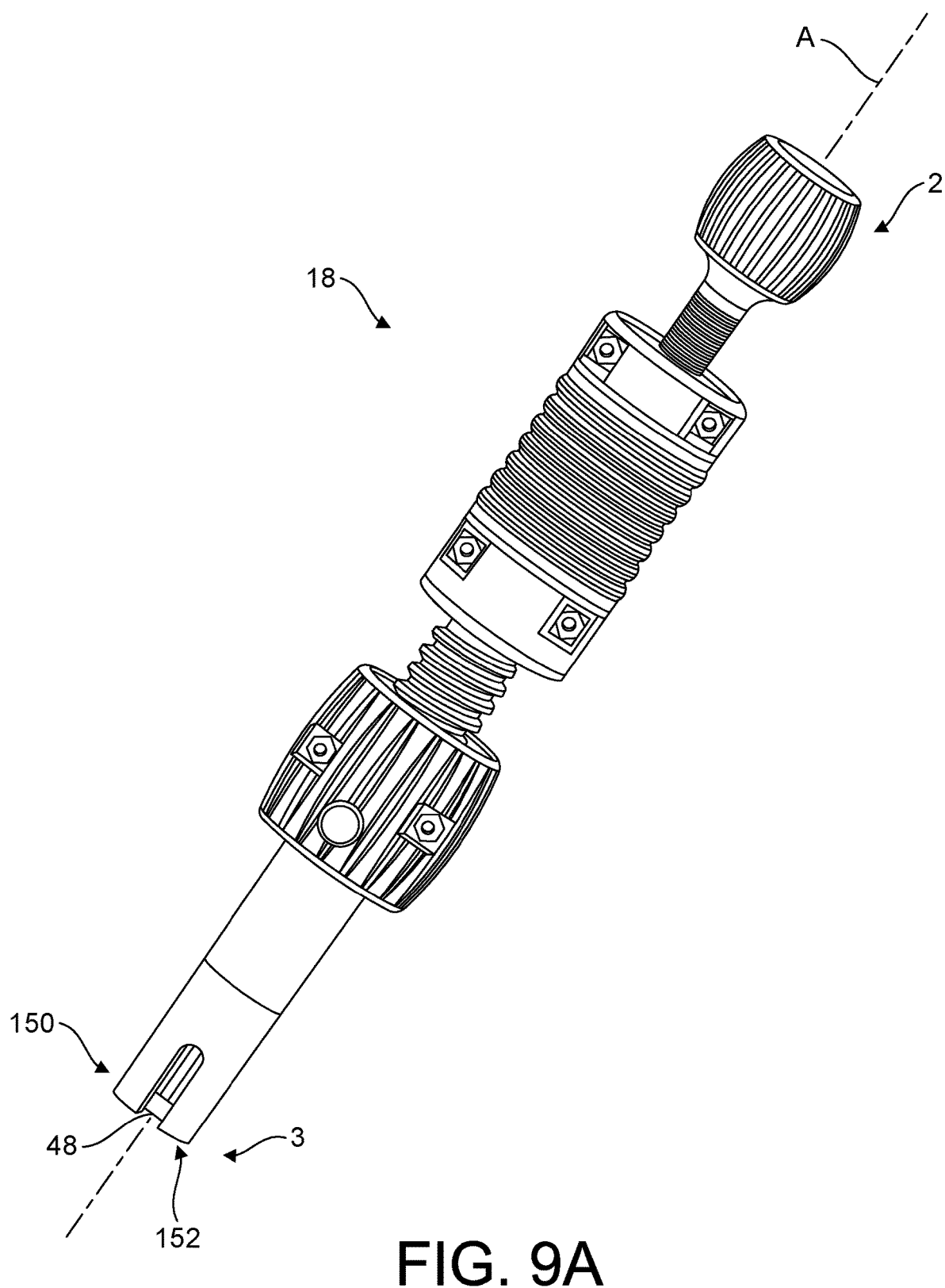
FIG. 9A is a perspective view of the example tool of FIG. 2.
Figure 12A:
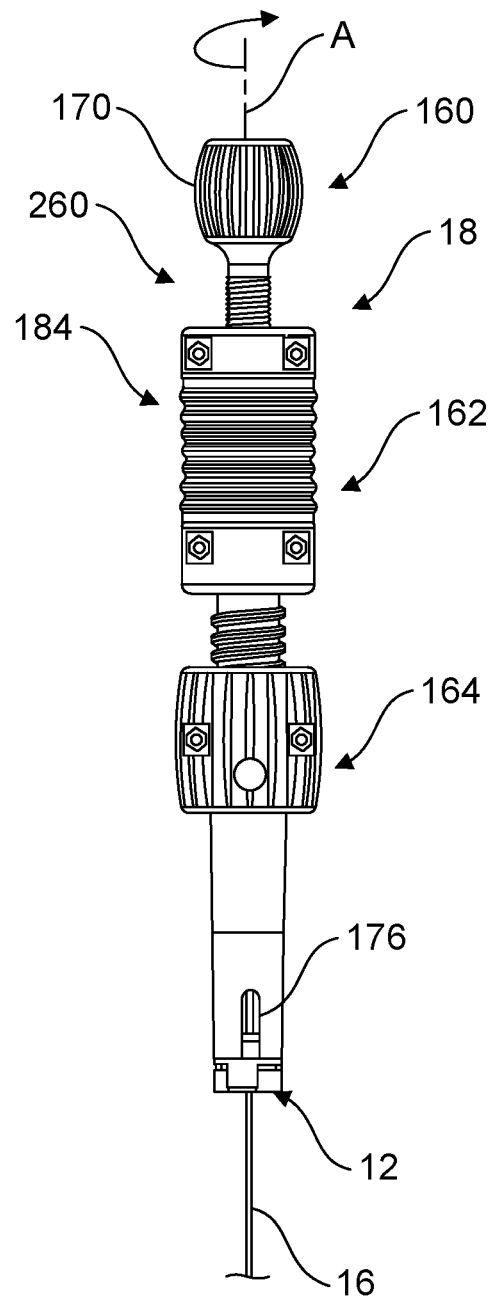
Figure 12B:
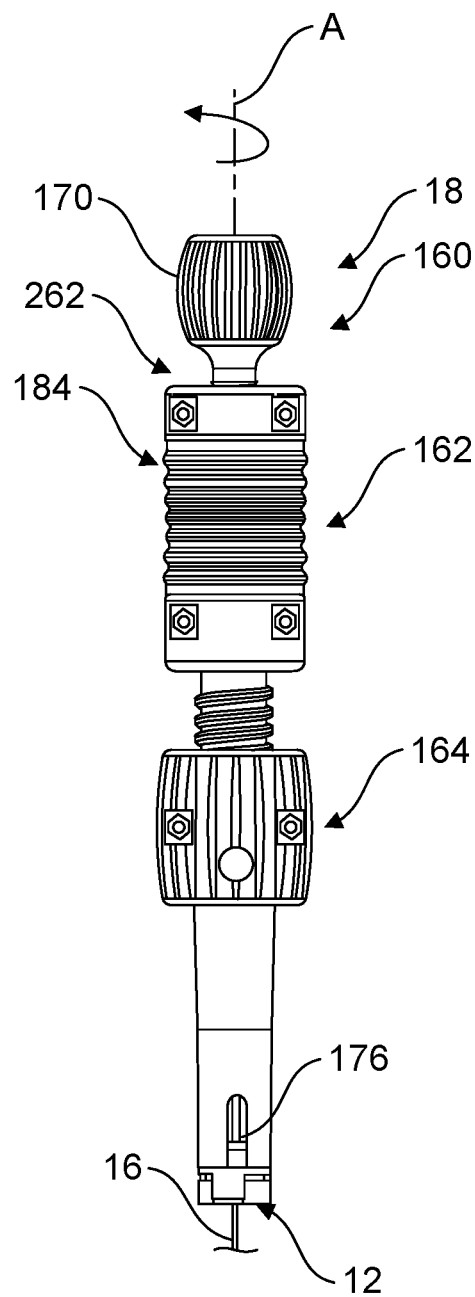
Figure 12C:
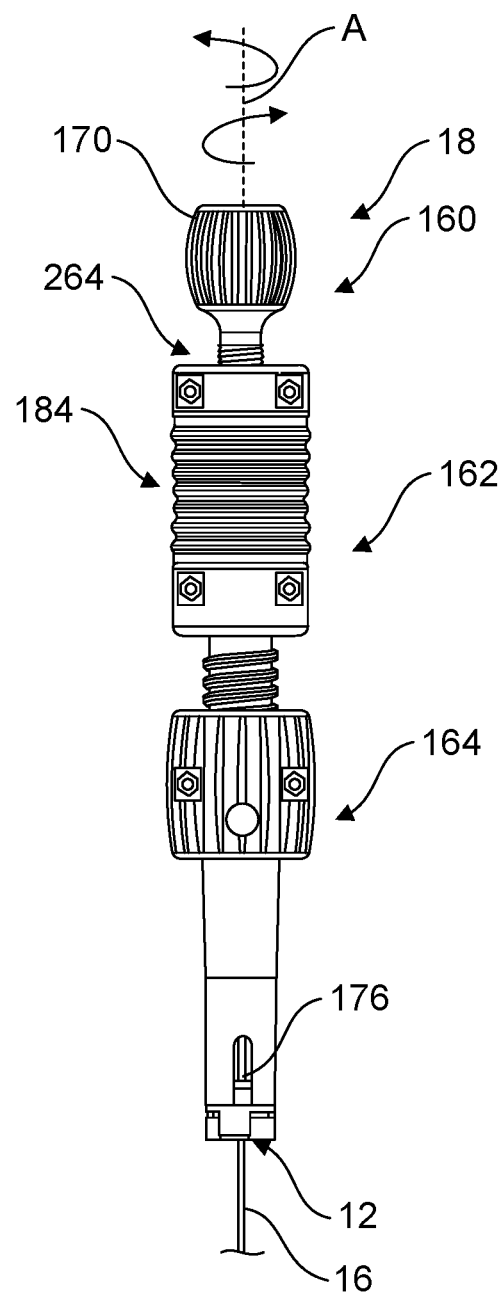

FIGS. 12A-12C are side views of the system of FIG. 2 illustrating example positions of the tool of FIG. 9A.

Figure 13A:
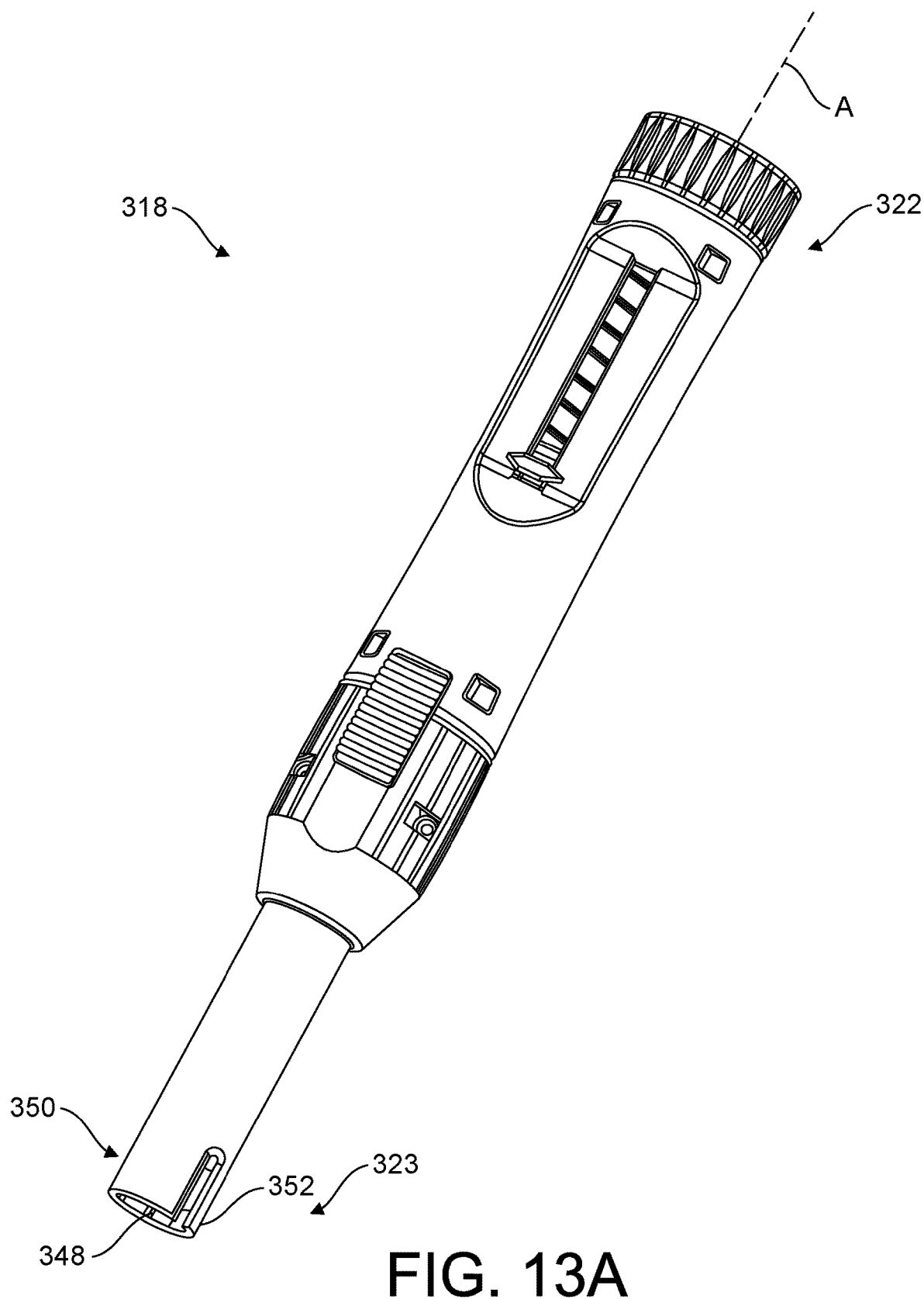

FIG. 13A is a perspective view of another example tool for use in the system of FIG. 2.

Figure 13B:
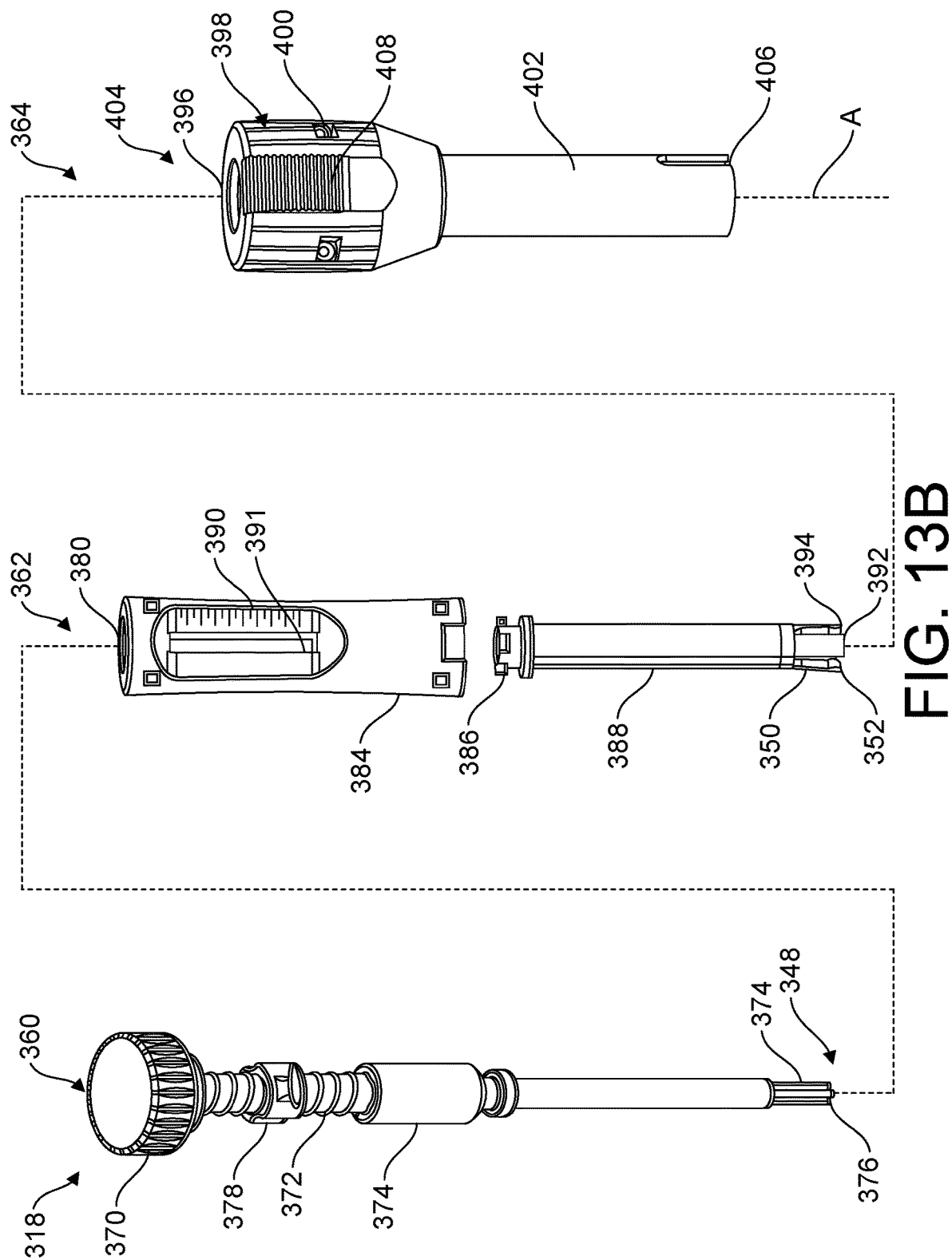

FIG. 13B is an exploded view of the example tool of FIG. 13A.

Figure 14A:
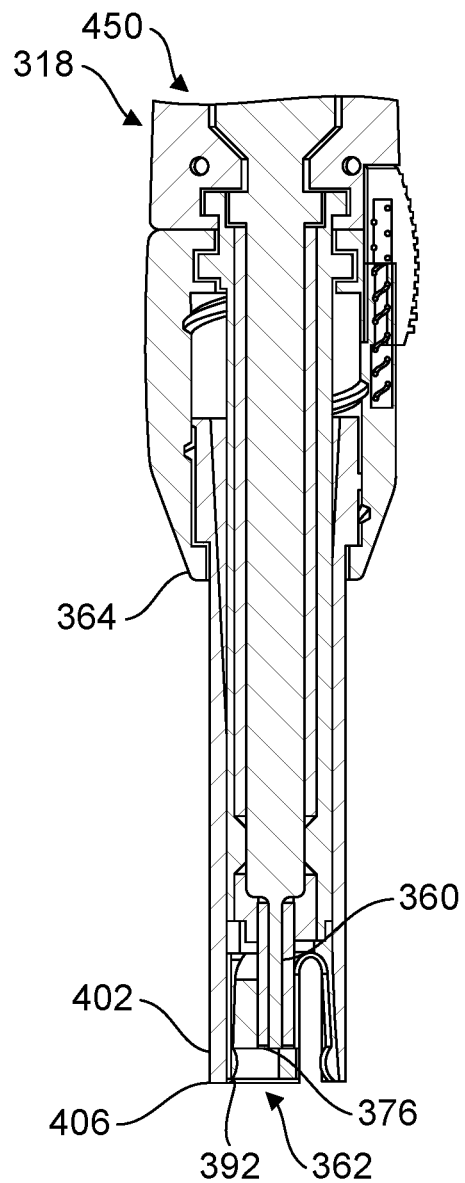

FIG. 14A is a side sectioned view of the example tool of FIG. 13A in a coupling configuration.

Figure 14B:
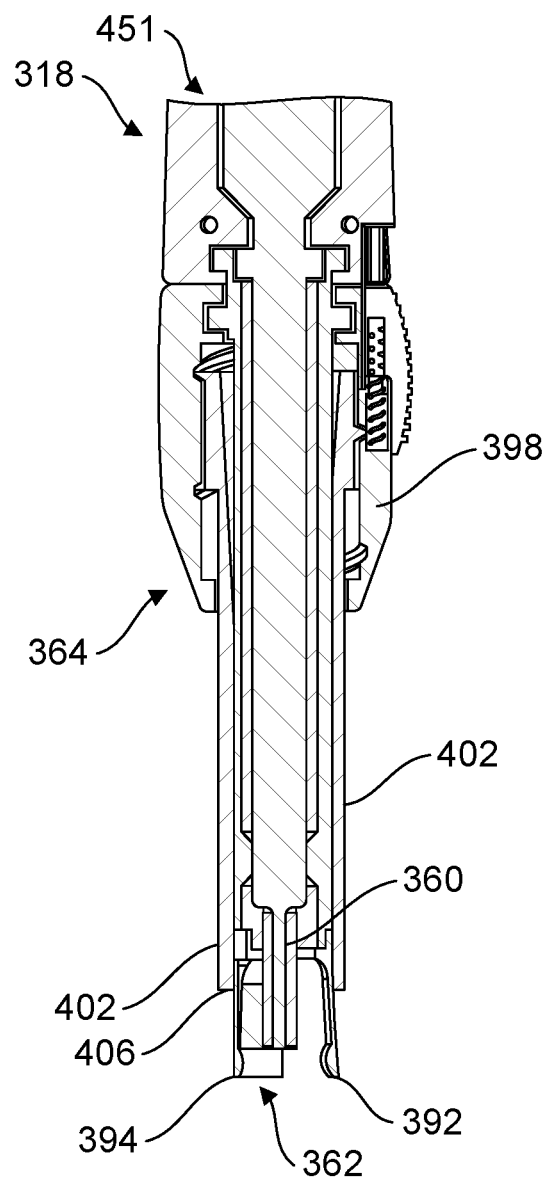

FIG. 14B is a side sectioned view of the example tool of FIG. 13A in an intermediate configuration.

Figure 14C:
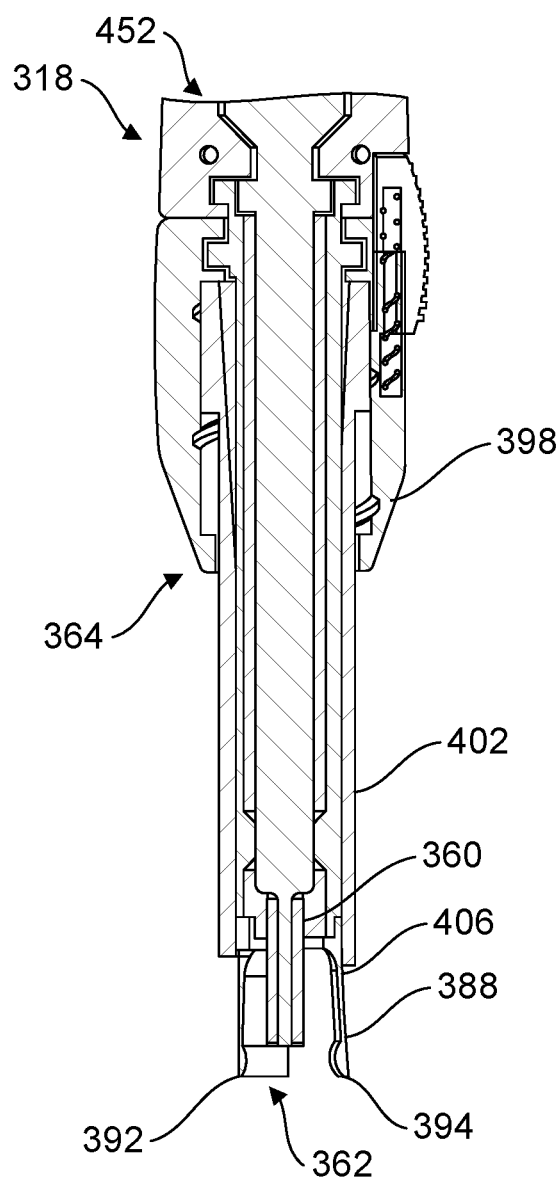

FIG. 14C is a side sectioned view of the example tool of FIG. 13A in a decoupling configuration.

FIGS. 15A-15D are side views of the tool of FIG. 13A illustrating an example method of transforming from the coupling configuration of FIG. 14A to the intermediate configuration of FIG. 14B to the decoupling configuration of FIG. 14C.

While the invention is amenable to various modifications and alternative forms, specific embodiments have been shown by way of example in the drawings and are described in detail below. The intention, however, is not to limit the invention to the embodiments described. On the contrary, the invention is intended to cover all modifications, equivalents, and alternatives falling within the scope of the invention as defined by the appended claims.

DETAILED DESCRIPTION

For purposes of promoting an understanding of the principles of the present disclosure, reference is now made to the examples illustrated in the drawings, which are described below. The illustrated examples disclosed herein are not intended to be exhaustive or to limit the disclosure to the precise form disclosed in the following detailed description. Rather, these exemplary embodiments were chosen and described so that others skilled in the art may use their teachings. It is not beyond the scope of this disclosure to have a number (e.g., all) the features in a given example used across all examples. Thus, no one figure should be interpreted as having any dependency or requirement related to any single component or combination of components illustrated therein. Additionally, various components depicted in a given figure may be, in examples, integrated with various ones of the other components depicted therein (and/or components not illustrated), all of which are considered to be within the ambit of the present disclosure.

The terms "couples," "coupled," "connected," "attached," and the like along with variations thereof are used to include both arrangements wherein two or more components are in direct physical contact and arrangements wherein the two or more components are not in direct contact with each other (e.g., the components are "coupled" via at least a third component), but yet still cooperate or interact with each other.

Throughout the present disclosure and in the claims, numeric terminology, such as first and second, is used in reference to various components or features. Such use is not intended to denote an ordering of the components or features. Rather, numeric terminology is used to assist the reader in identifying the component or features being referenced and should not be narrowly interpreted as providing a specific order of components or features.

Figure 1:
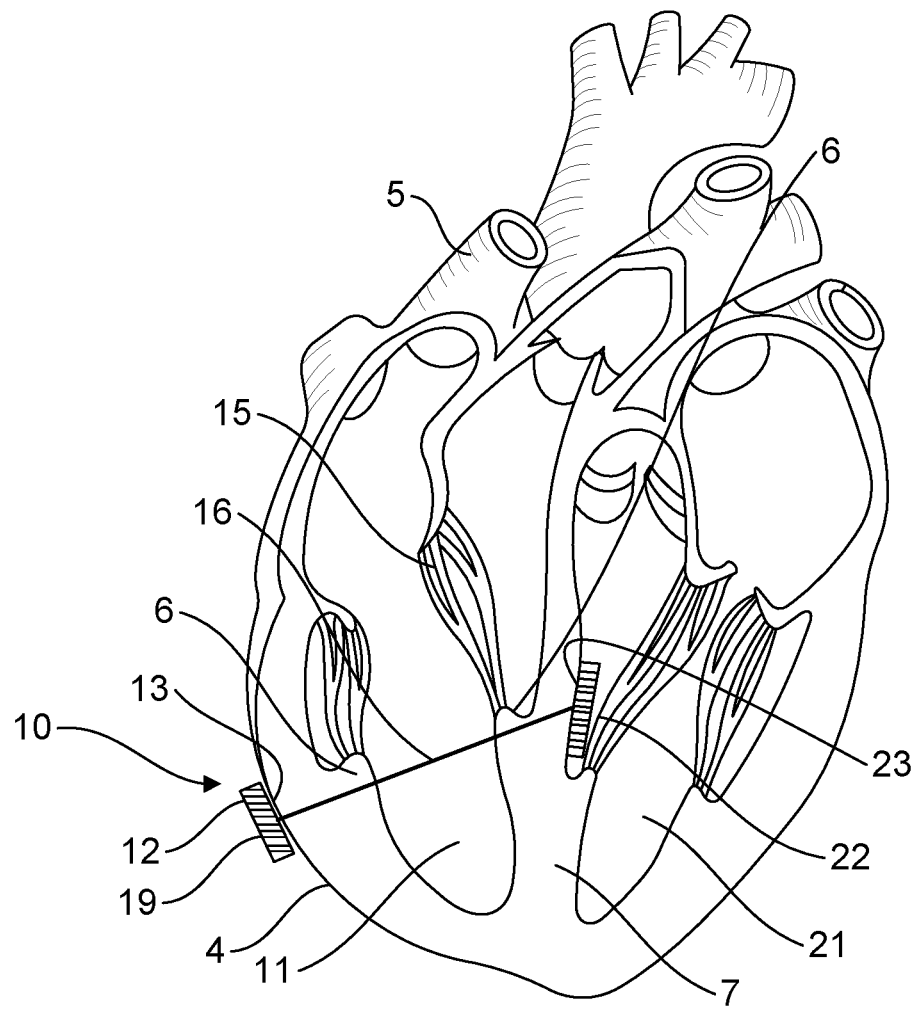
FIG. 1 is schematic diagram illustrating an example valve repair assembly implanted in a patient's heart of the present disclosure.

FIG. 1 is a schematic view illustrating an example implantable assembly 10 for reshaping a heart chamber, such as for example a right or a left ventricle 11, 21 in a patient. The implantable assembly 10 comprises at least one tether 16 and a first anchor (e.g., an active anchor) 12. As shown in FIG. 1, the implantable assembly 10 is adapted to reshape the right ventricle 11 of a patient's heart 5, for example, to treat the tricuspid valve 15. According to other examples, the implantable assembly 10 is adapted to reshape the left ventricle 21 of a patient's heart, for example to treat the mitral valve.

The active anchor 12 comprises an abutment portion 13 adapted to abut against a structure of the ventricle 11, 21, such as a wall of the heart that delimits or is located inside the ventricle. The structure of the ventricle 11, 21 can include an outer wall 4 of the patient's heart 5 delimiting the ventricular chamber or a papillary muscle 6 or an interventricular septum 7 of the heart 5. For example, the structure of the ventricle 11 is an outer wall 4 of the patient's heart 5 delimiting the ventricular chamber 11 so that the abutment portion 13 of the active anchor 12 of the implantable assembly 10 is adapted to abut against the outer wall 4 of the heart 5.

As shown, the abutment portion 13 of the active anchor 12 is outside the right ventricle 11 and abuts against the outer wall 4 of the heart 5. The tether 16 crosses the right ventricle 11 to connect to a second structure of the right ventricle 11, for example a wall of the interventricular septum 7 or a wall of a papillary muscle 6 of the right ventricle 11. The implantable assembly 10 can also be implanted in a left ventricle 21 to reshape the left ventricle 21 for the treatment of the mitral valve.

In various embodiment, the assembly 10 further includes a second anchor (e.g., a septal anchor) 22, which is disposed opposite the first anchor 12 with the tether 16 connected therebetween. The second anchor 22 also comprises a second abutment portion 23 adapted to abut against a second structure of the right ventricle 11, opposite to the first structure of the right ventricle 11 where the active anchor 12 abuts, so that the active anchor 12 and the second anchor 22 have respective abutment portions 13, 23 opposite to each other and so that the tether 16 can exert a traction action between the two anchors 12, 22, consequently causing the reshaping of the ventricles 11, 21. In accordance with an embodiment, the second anchor 22 comprises a portion, for example a hook, for coupling to a second ventricle structure. For example, the abutment portion 23 of the second anchor 22 is intended to abut against a wall facing the left ventricle 21 of the interventricular septum 7 so that the second anchor 22 is in the left ventricle 21, the first anchor 12 is on the wall 4 of the heart 5 and the tether 16 extends from the first anchor 12 to the second anchor 22. In accordance with an embodiment, the second anchor 22 is different from the first anchor 12. For instance, the second anchor 22 can be a passive anchor, i.e., it is unable to adjust the tensional state of the tether 16. While the first anchor 12 is described below as the active anchor, in various embodiments, the second anchor is an active anchor and the first anchor is a passive anchor. Moreover, in various embodiments both anchors 12, 22 are active anchors.

The active anchor 12 of the implantable assembly 10 is adapted to adjust the tensional state of the tether 16 via adjustment device 19. In various embodiments, the tensional state of the tether 16 is adjusted by varying the length of the tether 16 between the abutment portion 13 of the first anchor 12 and the abutment portion 23 of the second anchor 22, i.e., the working length of the tether 16 between the two anchors 12, 22. Adjusting the tensional state of the tether 16 can lead to a change in the useful length of the tether 16. Adjusting the tensional state of the tether 16 allows to adjust the traction force between the two anchors 12, 22. Adjusting the tensional state of the tether 16 allows to adjust the relative position of the abutment portions 13, 23 of the two anchors 12, 22, which in turn adjusts the distance between the corresponding structures of the ventricle.

The tether 16 can comprise an elastic element, to provide an elastic influence action aimed at bringing the two anchors 12, 22 closer together or aimed at distancing the two anchors 12, 22 away from each other. The tether 16 can comprise at least one section made of shape-memory material. At least one anchor 12 or 22 of the two anchors 12, 22 can comprise at least one portion made of shape-memory material.

FIG. 2 is a schematic view illustrating the example implantable assembly 10 in combination with a tool 18 to form a system 1 for reshaping the ventricle 11, 21. The tool 18 is non-implantable and detachably connectable to the implantable assembly 10. The tool 18 comprises a proximal portion 2 and a distal portion 3 opposite to the proximal portion 2. A longitudinal axis A is defined between the proximal portion 2 and the distal portion 3 of the tool 18. The active anchor 12 of the implantable assembly 10 is adapted to be detachably connectable to the distal portion 3 of the tool 18. The distal portion 3 of the tool 18 comprises an adjustment mechanism (see, for example, the adjustment key 48 further described below with respect to FIG. 9) adapted to cooperate with the adjustment device 19 of the active anchor 12. Operation of the adjustment mechanism can adjust the tensional state of the tether 16 by means of the operation of the adjustment device 19.

The proximal portion 2 of the tool 18 comprises a maneuvering interface 42 that is operatively connectable to the adjustment key 48 for adjusting the tensional state of the tether 16 by acting on the maneuvering interface 42 of the proximal portion 2 of the tool 18. In one example, the maneuvering interface 42 is intended to remain outside the patient's body during the adjustment of the tensional state of the tether 16 while the distal portion 3 of the tool 18 is connected to the active anchor 12 inside the patient's body. The active anchor 12 can be placed on the outer wall 4 of the heart 5, preventing the tool 18 from having to penetrate inside the patient's heart 5 to adjust the tensional state of the tether 16.

Figure 3A:
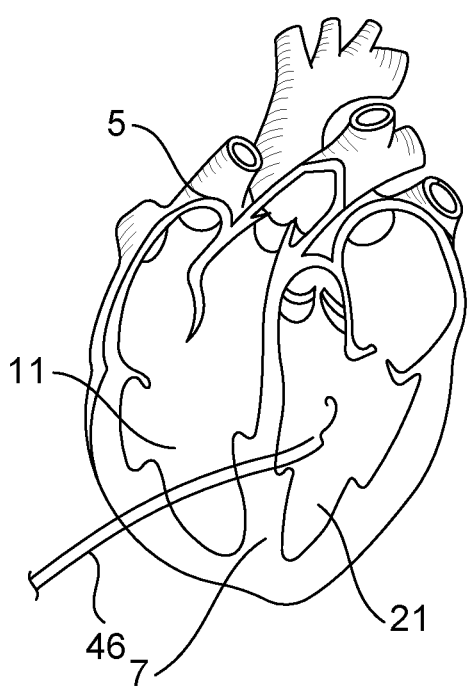
FIGS. 3A-3F are schematic diagrams illustrating an example method of implantation of the example valve repair assembly of FIG. 1 via use of the tool of FIG. 2.
Figure 3B:
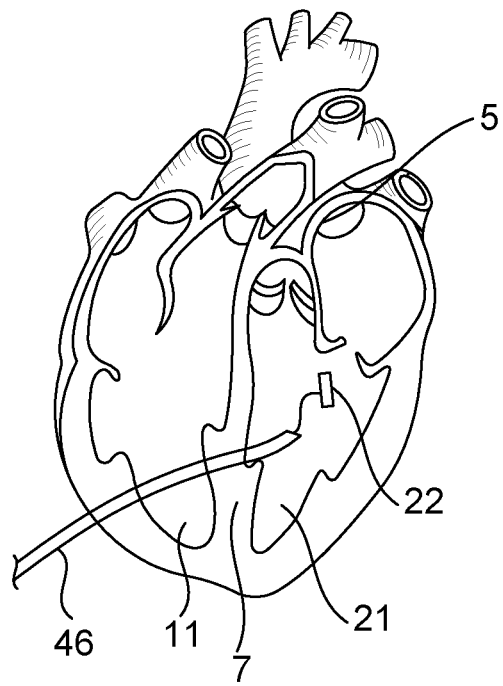
Figure 3C:
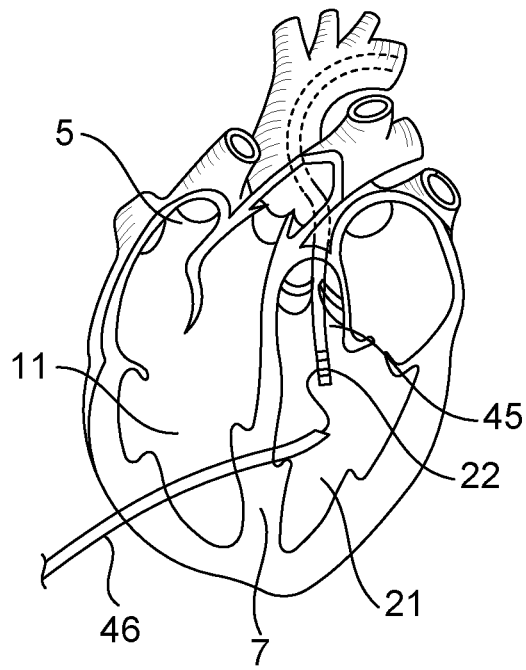
Figure 3D:
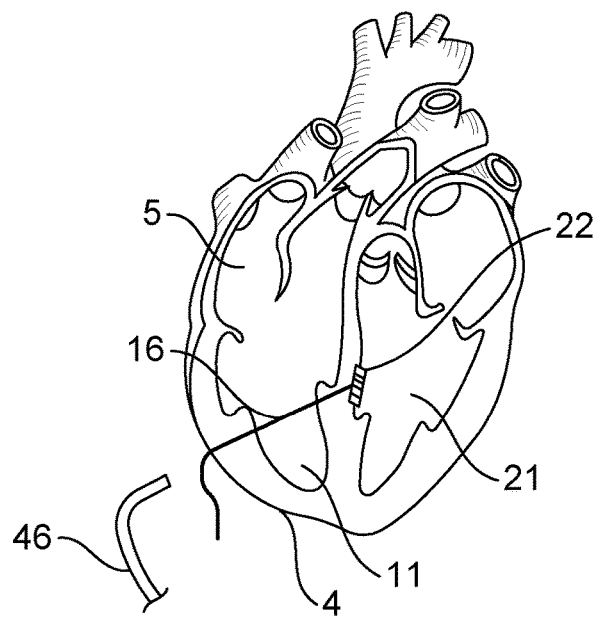
Figures 3E, 3F:
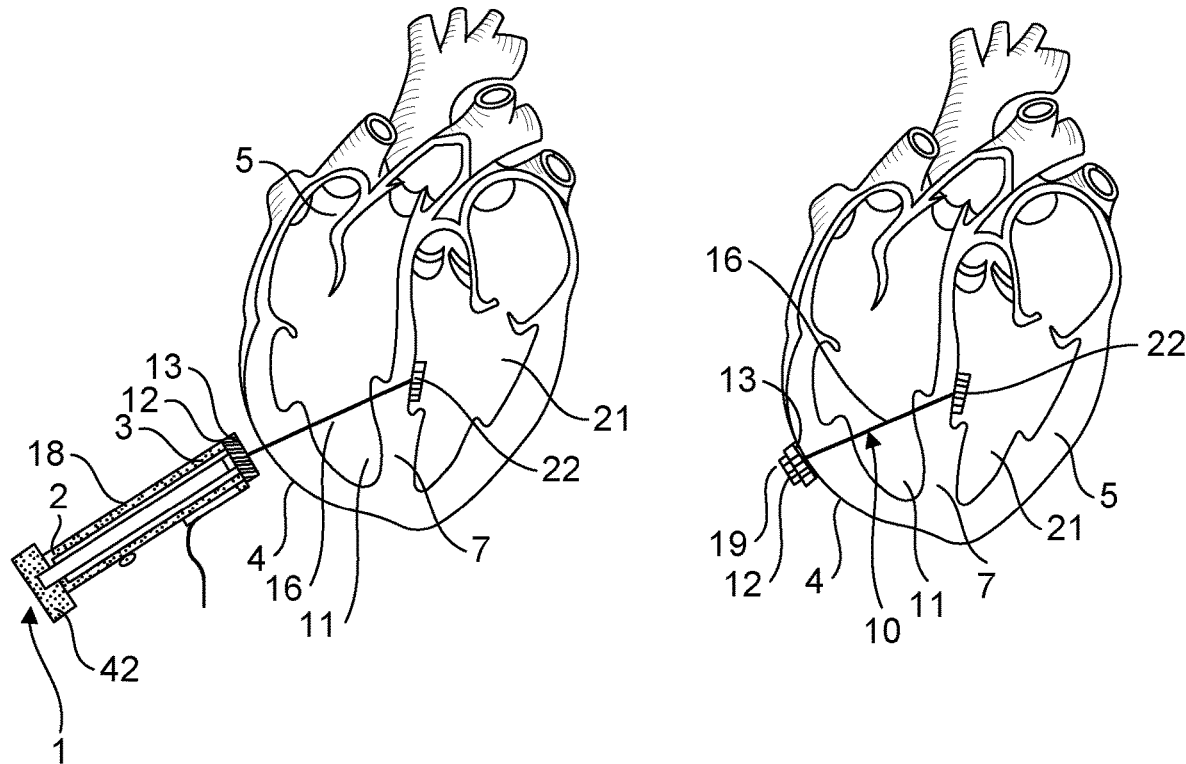

FIGS. 3A-3F illustrate a method to implant the implantable assembly 10 into the patient's heart 5 for treatment of the tricuspid valve 15. As shown in FIG. 3A, a delivery catheter 46 is advanced into the thoracic cavity, such as through an incision between or below a patient's ribs, and proximate the heart 5. The delivery catheter 46 is advanced such as over a guidewire through the outer wall 4, right ventricle 11, and the septum 7 to into the left ventricle 21. As shown in FIG. 3B, the delivery catheter 46 can carry the second anchor 22 and tether 16 to the corresponding implantation site such as the septum 7 in the left ventricle 21. As shown in FIG. 3C, a vascular catheter 45 can carry at least a portion of the implantable assembly 10, such as the second anchor 22 through the vasculature to the left ventricle 21. As illustrated in FIG. 3D, the second anchor 22 is disposed at the corresponding implantation site against the septum 7 in the left ventricle 21, and the tether 16 is extended across the right ventricle 11 and through the wall 4. As illustrated in FIG. 3E, the active anchor 12 can be delivered on the outer wall 4 of the heart 5 by the tool 18, for example mounted on the distal end 3 of the tool 18. The tool 18 acts as a delivery device at least for the active anchor 12 of the implantable assembly 10.

As illustrated in FIG. 3F, the tensional state of the tether 16 can be adjusted at the active anchor 12 before detachment from the tool 18. The tool 18 is configured to adjust the tensional state of the tether 16 of the implantable assembly 10 by activating the adjustment device 19 of the active anchor 12 from outside the heart 5. The inclusion of such a tool 18 allows for the adjustment of the tensional state of the tether 16 both during the implantation of the implantable assembly 10 and in a procedure after the implantation that avoids having to access inside the patient's heart 5.

Figure 4:
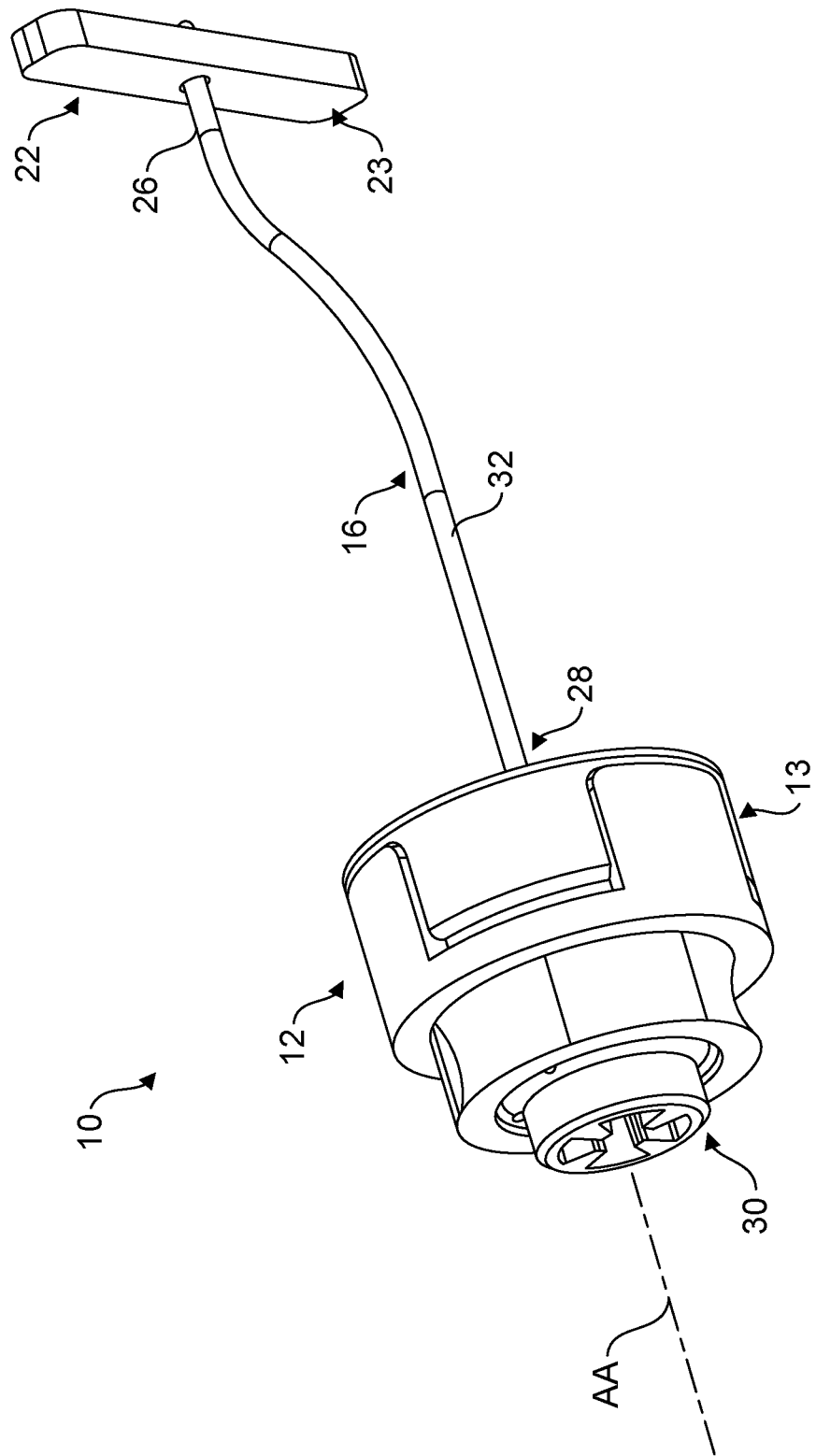
FIG. 4 is a perspective view of the example valve repair assembly of FIG. 1.
Figure 5A:
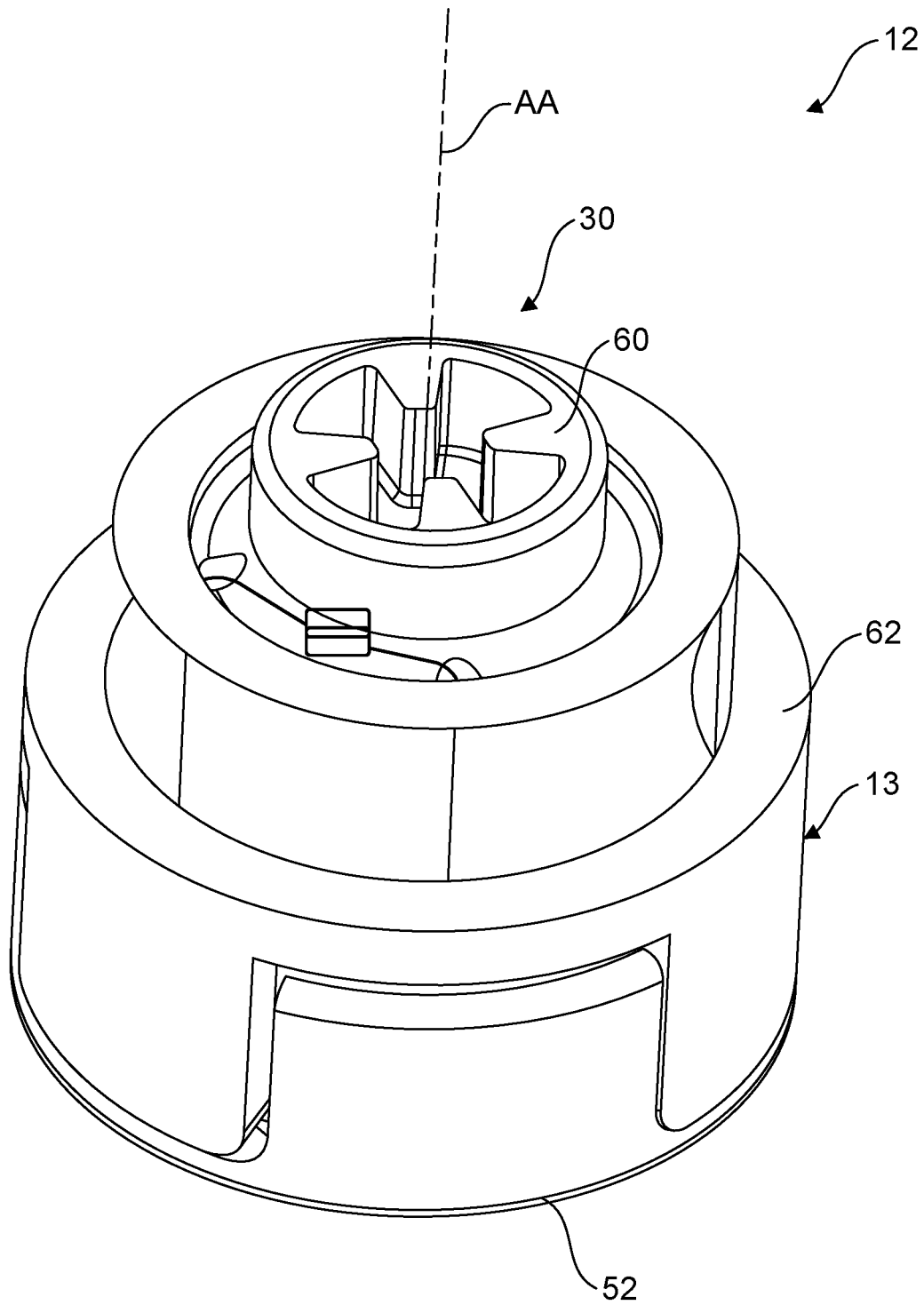
FIG. 5A is a perspective view of an example, active anchor of the example valve repair assembly of FIG. 1.
Figure 5B:
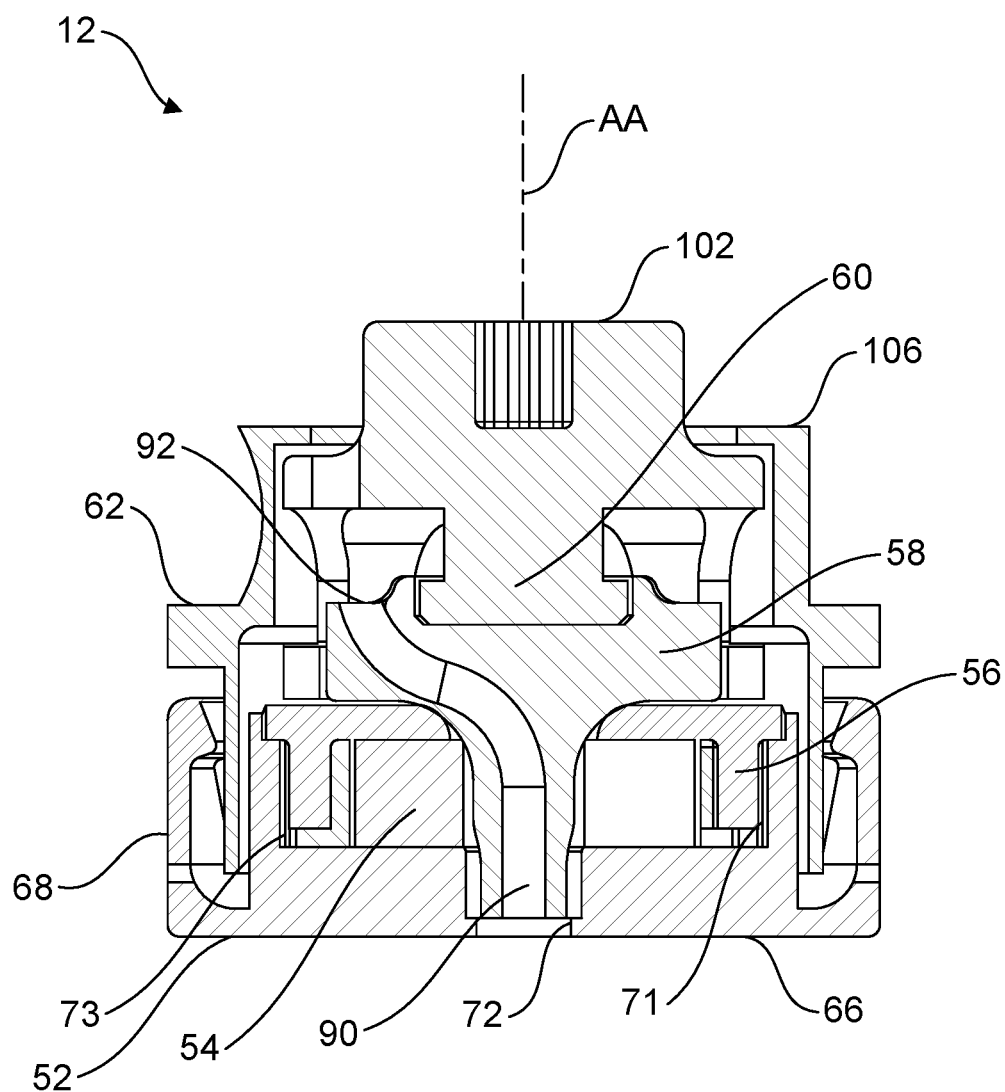
FIG. 5B is a side sectioned view of the example active anchor of FIG. 5A.
Figure 5D:
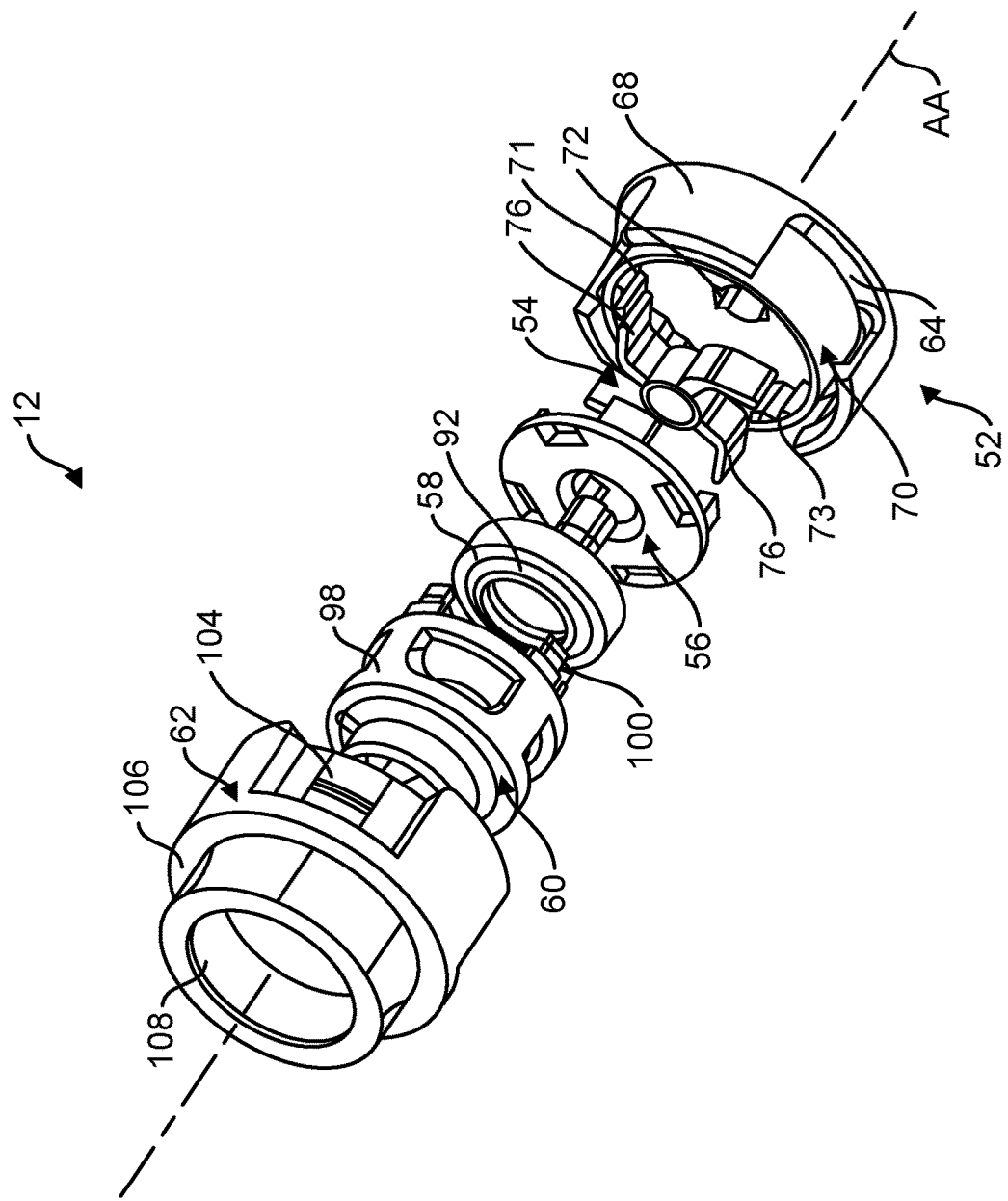
FIG. 5D is an exploded view of the example active anchor of FIG. 5A from a second perspective.

FIG. 4 illustrates the implantable assembly 10. The assembly 10 is adapted to reshape a cardiac chamber of the heart 5, such as the right ventricle 11, to accomplish a repair of a heart valve. The implantable assembly 10 includes a first anchor (e.g., active anchor) 12, a tether 16, and a second anchor 22, or septal anchor 22. The tether 16 can include a first end 26 coupled to the septal anchor 22 and a second end 28 coupled to the active anchor 12. The septal anchor 22 includes the abutment portion 23 configured to touch against the septum 7 when implanted. As shown, the septal anchor 22 includes a hole to receive the tether 16 through the abutment portion 23, and the first end 26 of the tether 16 can be fixedly attached to the septal anchor 22 via a knot or fixing mechanism. The active anchor 12 includes the abutment portion 13 adapted to touch against a wall of the right ventricle 11. The active anchor 12 also includes a tether portion 30 rotatably coupled to the abutment portion 13. The tether portion 30 is also fixedly coupled to the second end 28 of the tether 16. The tether 16 includes a working portion 32 extending between the active anchor 12 and the septal anchor 22. A portion of the tether 16 is housed inside the tether portion 30 of the active anchor 12. In various embodiments, the proximal portion (not shown) of the tether 16 is wound around the tether portion 30 of the active anchor 12. The abutment portion 13 is releasably locked to the tether portion 30 and configured such that a predetermined or preselected torque applied to the tether portion 30 unlocks the portions 13, 30 and causes relative rotation of the portions 13, 30 about axis AA.

The rotation adjusts the first length of the working portion 32 of the tether 16 and the second length of the proximal portion. In one example, the active anchor 12 is configured to allow the relative rotation to occur in both directions, such as rotation in a first direction about the axis AA and rotation in a second, opposite direction about the axis AA. In the first direction, the first length of the working portion 32 of the tether 16 is shortened, such that the septal anchor 22 and the active anchor 12 are pulled toward each other, and the second length of the proximal portion of the tether 16 is lengthened as the tether portion 30 takes up more of the tether 16. In the second direction, the first length of the working portion 32 of the tether 16 is lengthened, such that the septal anchor 22 and the active anchor 12 may move apart from each other, and the second length of the proximal portion of the tether 16 is reduced as the tether portion 30 gives up more of the tether 16.

FIGS. 5A-5D illustrate components of an example active anchor 12 having tether portion 30 rotatably coupled to the abutment portion 13 about axis AA. As shown, the active anchor 12 includes a housing 52, a lock member 54, a biasing member 56, a shaft 58, a spool 60, and an outer case 62 disposed about axis AA. The housing 52 includes a plate member 64 having a outer abutment surface 66, locking clips 68, and ring remember 70 attached to and upstanding on plate member 64 opposite the abutment surface 66. The ring member 70 can include a textured inner surface 71, such as teeth 73. The plate member 64 forms an axially-disposed aperture 72 through the housing 52. The lock member 54 includes a hub 74 and a plurality of wings 76, such as four wings 76, radially extending from the hub 74 at a length to fit against an inner surface 71 of the ring member 70. In some examples, the wings 76 engage with the teeth 73 of the inner surface 71. The biasing member 56 includes a plate member 78 forming an axially disposed aperture 80 and a plurality of slots 82 through the plate member 78. The plate member 78 includes a first surface having a plurality of radially spaced arms 84 configured to engage the wings 76 of the lock member 54.

According to various embodiments, the shaft 58 includes an axially-disposed spout 86 and a funnel 88. As shown, the funnel 88 includes a wider diameter than the spout 86. In various embodiments, the spout 86 is configured to extend through the aperture 80 of the biasing member 56, the hub 74 of the lock member 54 and into the aperture 72 of the housing 52. This configuration functions to impede relative rotation of the shaft 58 with respect to the housing 52. The shaft 58 further defines a bore 90 extending from the spout 86 to an off-axis port 92 on a top surface 94 of the funnel 88. The spool 60 includes an axial winding shaft 96 disposed within a cage 98 having legs 100 and an axially disposed anchor back 102 on an opposite end of the active anchor 12 with respect to the outer abutment surface 66. In certain embodiments, the anchor back 102 is disposed parallel to the abutment surface 66.

The cage 98 is disposed to fit around the funnel 88, and the spool 60 can freely rotate about the axis with respect to the shaft 58. The legs 100 are configured to fit within the slots of the 82 on the plate member 78 of the biasing member 56 such that the spool 60 and biasing member 56 rotate together about the axis AA and with respect to the shaft 58. The outer case 62 is configured to attach to the housing 52 and encase the engaging member 54, biasing member 56, shaft 58, and spool 60. For example, the outer case 62 includes tabs 104 to mate with and attach to locking clips 68 of the housing 52. The outer case 62 further includes an upper surface 106 with an opening 108 to receive the spool 60 such that the anchor back 102 extends through the outer case 62. The opening 108 is configured to permit the spool 60 freely rotate about the axis AA within the outer case 62.

In various embodiments, the housing 52, shaft 58, and outer case 62 of the active anchor 12 form the components of the abutment portion 13. The housing 52 is configured to abut against the wall 4 of the heart 5, and the shaft 58 and outer case 62 are coupled to the housing 52 and do not rotate with respect to each other. The lock member 54, biasing member 56, and spool 60 form components of the tether portion 30 and rotate together. The components of the tether portion 30 can rotate together and rotate with respect to the components of the abutment portion 13. As shown, the components of the tether portion 30 do not move axially with respect to the components of the abutment portion 13.

The active anchor 12 includes a locked configuration and an unlocked configuration. In the locked configuration, the components of the abutment portion 13 do not rotate with respect to the components of the tether portion 30. In the unlocked configuration the components of the tether portion 30 rotate about the axis AA with respect to the components of the abutment portion 13. The locked configuration is a default configuration for the active anchor 12. A selected toque applied to the components of the tether portion 30 with respect to the components of the abutment portion 13, such as with the tool 18, imparts the unlocked configuration. As shown, the lock member 54, which is coupled to rotate with the biasing member 56 and spool 60, yieldably engages the housing 52 such that under typical conditions the components of the tether portion 30 do not rotate with respect to the components of the abutment portion 13. For example, the wings 76 of the lock member 54 are deflectable under a selected threshold torque and yieldably urged against the inner surface 71 of the ring member 70 of the housing 52 to form an interference fit or engage with the teeth 73. The arms 84 of the biasing member 56 engage the wings 76 of the lock member 54. The spool 60 is coupled to the biasing member 56. The spool 60 is configured to receive a torque with respect to the components of the abutment portion 13, such as from the tool 18, and transfer the torque to the biasing member 56.

The interference fit of the wings 76 and the teeth 73 will prevent the components of the tether portion 30 from rotating with respect to the components of the abutment portion 13 unless and until the biasing member 56 is subjected to a torque above the selected threshold torque. If the torque from the tool 18 on the spool 60 surpasses the threshold, the arms 84 of the biasing member 56 will deflect the wings 76 of the lock member 54 such that the wings 76 are no longer pressed against the inner surface 71 or teeth 73 of the ring member 70 enough to hold the lock member 54 in place with the housing 52. Accordingly, the components of the tether portion 30 can rotate about the axis AA with respect to the components of the abutment portion 13. In various embodiments of the lock member 54, the components of the tether portion 30 can rotate about the axis AA with respect to the components of the abutment portion 13. According to various embodiments of the lock 54, the threshold torque is only necessary to permit rotation. Once the torque that surpasses the threshold torque is removed, the active anchor 12 automatically transitions to the locked configuration again with the wings 76 urged against the inner surface 71 or teeth 73 of the ring member 70 to prevent the components of the tether portion 30 from rotating with respect to the abutment portion 13.

Within the active anchor 12, the tether 16 can be wound around the spool 60 or, more specifically, around the winding shaft 96, to store the proximal portion (not shown) of the tether 16. When the active anchor 12 is in the unlocked configuration, and the tether components 30 are rotated in the first direction with respect to the abutment components 13, the first length of the working portion 32 of the tether 16 is shortened, such that the septal anchor 22 and the active anchor 12 are pulled toward each other, and the second length of the proximal portion of the tether 16 is lengthened as the tether portion 30 takes up more of the tether 16. When the active anchor 12 is in the unlocked configuration, and the tether components 30 are rotated in the second direction (i.e., the opposite direction), the first length of the working portion 32 of the tether 16 is lengthened, such that the septal anchor 22 and the active anchor 12 may move apart from each other, and the second length of the tether 16 is reduced as the tether portion 30, and in particular the winding shaft 96 of the spool 60, gives up more of the tether 16. When the active anchor 12 is in the locked configuration, the first length of the working portion 32 of the tether 16 and the second length of the tether 16 do not change and are held in place.

In one example, the lock 54 can be configured in such a way that the threshold torque to rotate the spool 60 in the first direction is different than the threshold torque to rotate the spool 60 in the second direction. In one example, the threshold torque to wind the tether 16 on the winding shaft 96 is less than the threshold torque to unwind the tether 16 from the winding shaft 96. In this example, more torque is applied to deflect the wings 76 away from the teeth 73 in the second direction than the first direction.

FIGS. 6A-6F illustrate example methods to attach the tether 16 to the active anchor 12. FIGS. 6A to 6C illustrate a method using a support tether 116 attached to the active anchor 12 and to the tether 16. As shown in FIG. 6A, the support tether 116 is a separate component attached to the spool 60 (e.g., using a knot or a coupling mechanism) at a first end 118 and to the tether 16 (e.g., using a knot or a coupling mechanism) at a second, free second end 120. FIG. 6B illustrates the tether 16 threaded through the aperture 72 in the housing 52 and into the bore 90 of the spout 86 in the shaft 58. The tether 16 exits the bore 90 of the shaft 58 at the off-axis port 92 on the top surface 84 of the funnel 88. FIG. 6C illustrates the tether 16 extending from the off-axis port 92 is attached to the second end 120 of the support tether 116, via a coupling 117, such as a knot or coupling mechanism, to connect the tether 16 to the spool 60 such that the tether 16 can be wound around the winding shaft 96 during operation.

FIG. 6D illustrates an example in which the tether 16 is directly coupled to the spool 60. The tether 16 is threaded through the aperture 72 in the housing 52 and into the bore 90 of the spout 86 in the shaft 58. The tether 16 exits the bore 90 of the shaft 58 at the off-axis port 92 on the top surface 84 of the funnel 88. The tether 16 is directly coupled to the spool 60 either via a knot or a coupling mechanism 110. FIGS. 6E-6F illustrate an example in which the spool 60 includes a clasp member 122 to grasp and hold the tether 16. The tether 16 threaded through the aperture 72 in housing 52 and into the bore 90 of the spout 86 in the shaft 58. The tether 16 exits the bore 90 of the shaft 58 at the off-axis port 92 on the top surface 84 of the funnel 88. FIG. 6E illustrates the clasp member 122 open to receive the end of the tether 16, and FIG. 6F illustrates the clasp member 122 closed to hold the end of the tether 16 such that the tether 16 is fixedly coupled to the spool 60.

Figure 7A:
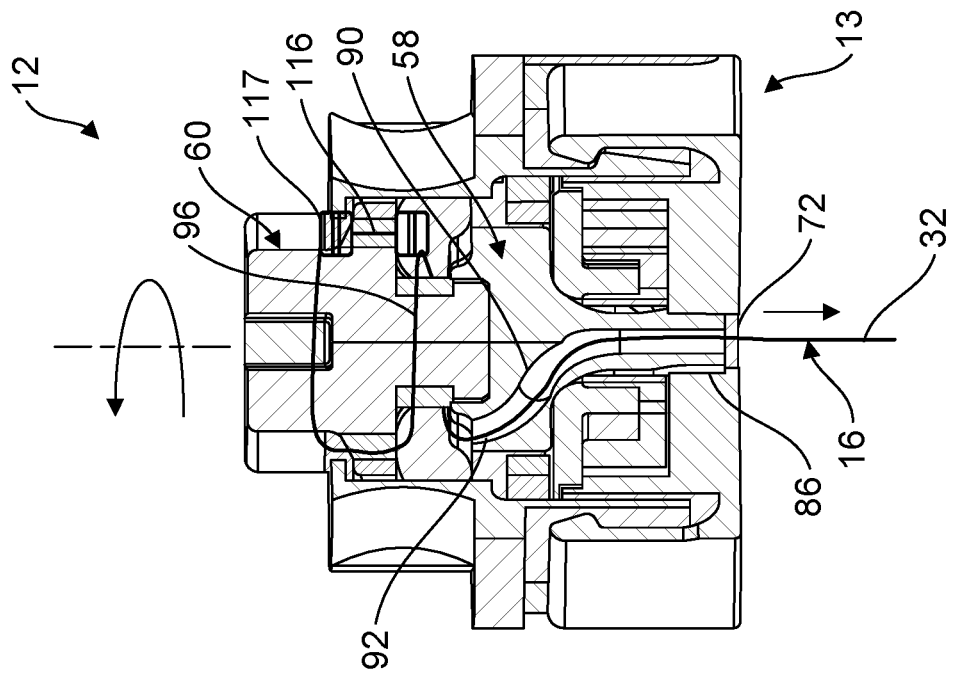
FIGS. 7A and 7B are side section views illustrating an example of the winding and unwinding of the tether to the example active anchor of FIG. 6C.
Figure 7B:
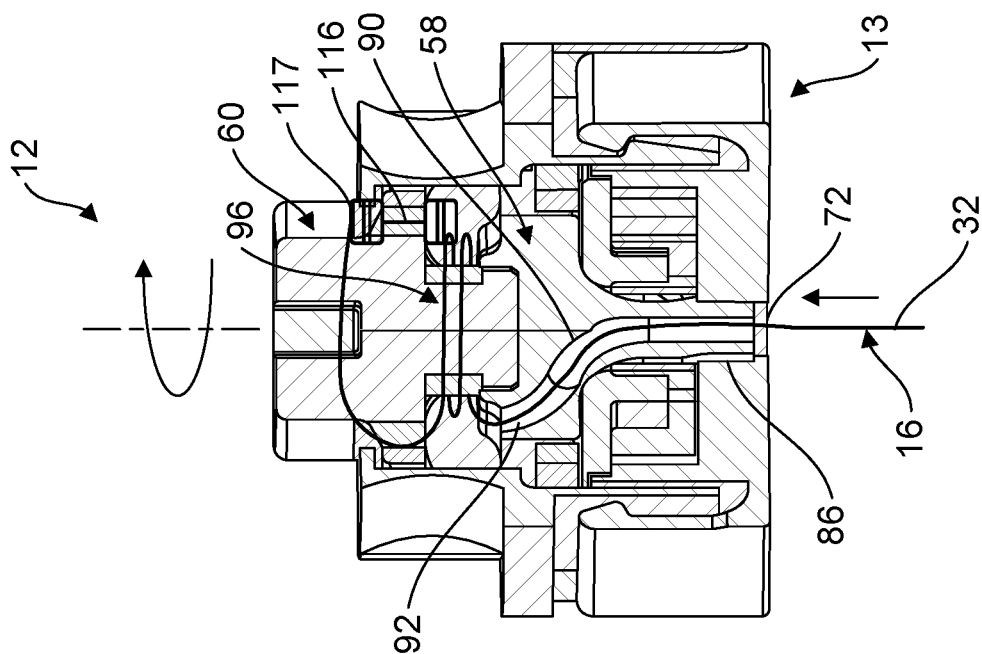
Figure 8A:
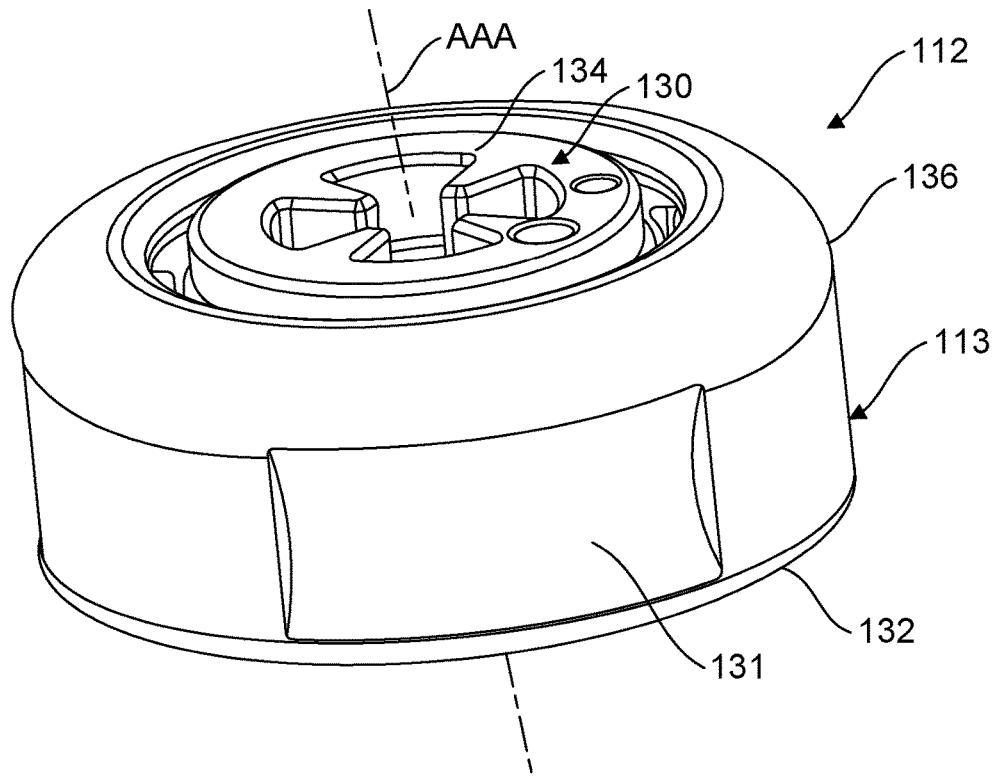
FIG. 8A is a perspective view of an example active anchor of the example valve repair assembly of FIG. 4 as an alternative to the active anchor of FIGS. 5A-5D.
Figure 8B:
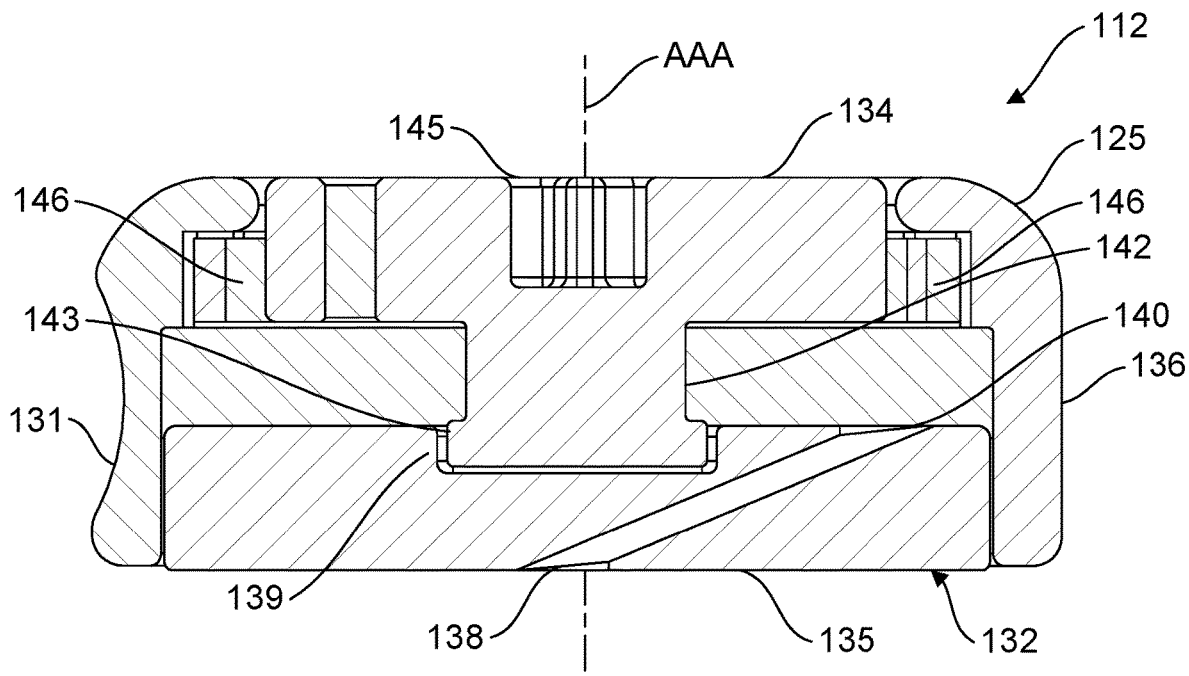
FIG. 8B is a side sectioned view of the example active anchor of FIG. 8A.
Figure 8C:
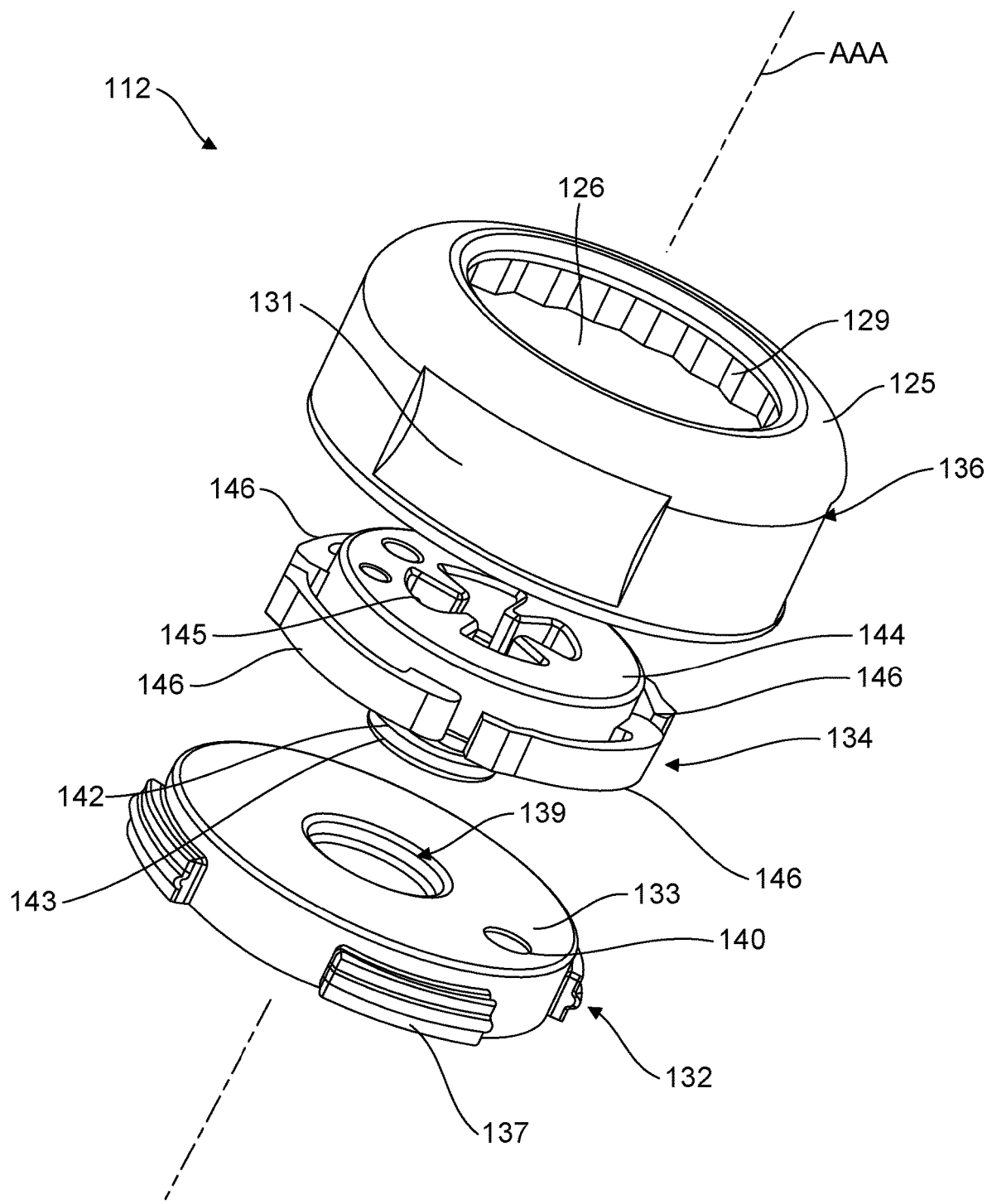
FIG. 8C is an exploded view of the example active anchor of FIG. 8A from a first perspective.
Figure 8D:
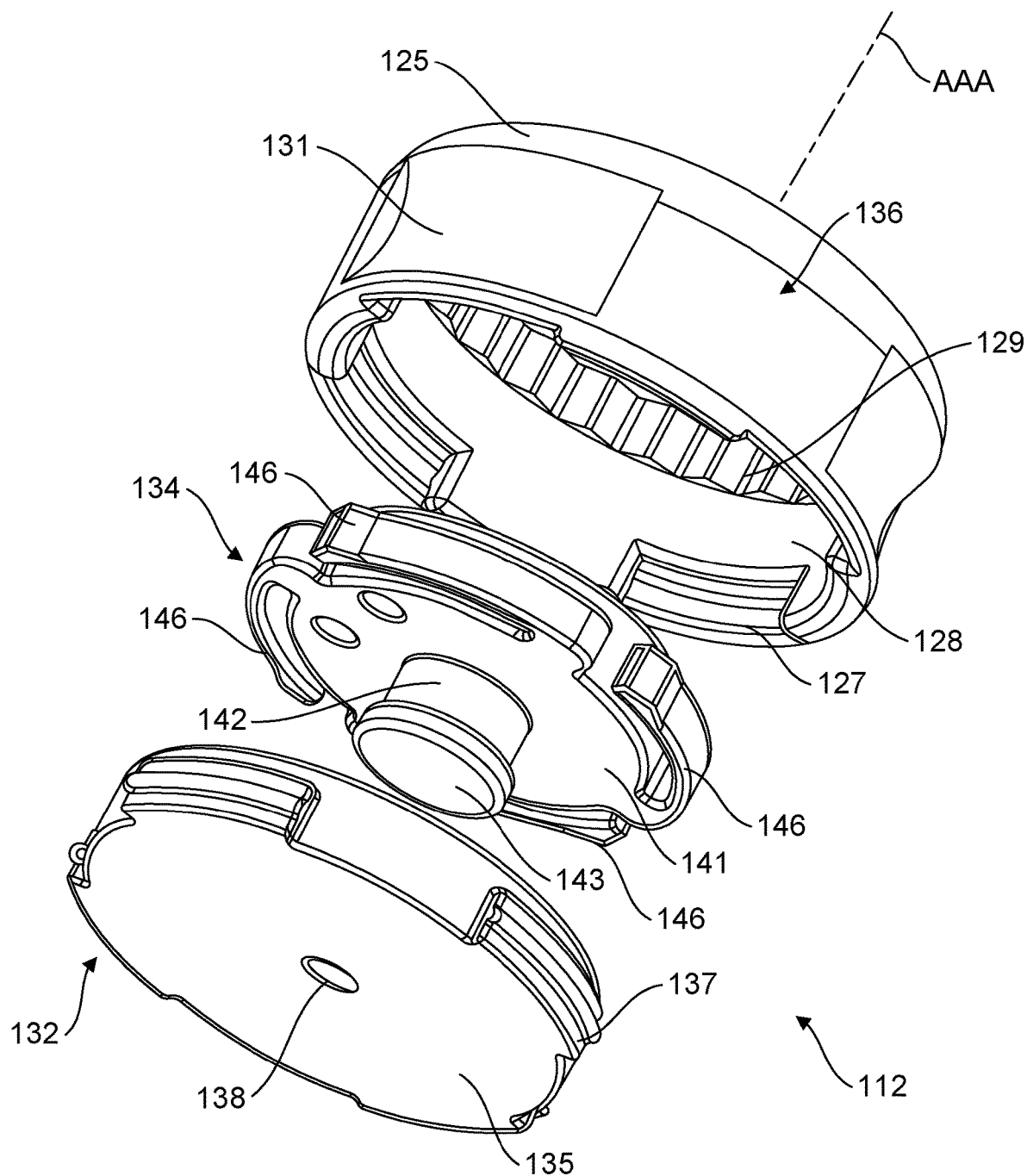
FIG. 8D is an exploded view of the example active anchor of FIG. 8A from a second perspective.

FIGS. 7A and 7B illustrate the winding and unwinding of the tether 16 within the active anchor 12. FIG. 7A illustrates support tether 116 coupled to tether 16 to attach the tether 16 to the spool 60. The tether 16 is threaded through the aperture 72 in housing 52 and into the bore 90 of the spout 86 in the shaft 58. The tether 16 exits the bore 90 of the shaft 58 at the off-axis port 92 on the top surface 84 of the funnel 88. As the spool 60 is rotated in a first direction, such as clockwise, with respect to the components of the abutment portion 13, the proximal portion of the tether 16 is wound onto the winding shaft 96. The first length of the working portion 32 of the tether 16 is shortened, and the second length of the tether 16 is lengthened as winding shaft 96 of the spool 60, takes up more of the tether 16.

FIG. 7B illustrates support tether 116 coupled to tether 16 to attach the tether 16 to the spool 60. The tether 16 is threaded through the aperture 72 in housing 52 and into the bore 90 of the spout 86 in the shaft 58. The tether 16 exits the bore 90 of the shaft 58 at the off-axis port 92 on the top surface 84 of the funnel 88. As the spool 60 is rotated in a second direction, such as counterclockwise, with respect to the components of the abutment portion 13, the tether 16 is unwound from the winding shaft 96. The first length of the working portion 32 of the tether 16 under traction is lengthened and the second length of the proximal portion of the tether 16 is reduced as the winding shaft 96 of the spool 60, gives up more of the tether 16.

FIGS. 8A-8D illustrate components of an exemplary active anchor 112 having a tether portion 130 rotatably coupled to abutment portion 113 about axis AAA, which can be included on assembly 10 in FIG. 4, instead of active anchor 12. The example active anchor 112 includes an abutment 132, a spool 134, and an outer case 136 disposed about the axis AAA. The abutment 132 includes an outer abutment surface 135, an opposite, inner surface 133, and locking clips 137. The outer abutment surface 135 includes a minor aperture 138 on axis AAA, and the inner surface 133 includes a major aperture 139 on axis AAA having a diameter larger then than the minor aperture 138. The inner surface 133 also includes an off-axis opening 140 in communication with the minor aperture 138. The spool 134 includes a first surface 141 coupled to an axial winding shaft 142 having a terminal disk 143. The terminal disk 143 as shown fits underneath the inner surface 133 to couple the spool 134 to the abutment 132 and allow the spool 134 to freely rotate about the axis AAA with respect to the abutment 132.

The spool 134 includes a second surface 144 having an anchor back 145 configured to mate with an adjustment mechanism of the tool 18. In the illustrated embodiment, the spool 134 further includes a plurality of circumferentially disposed deflectable wings 146 configured to engage the teeth 129 on an inner surface 128 of the outer case 136. The outer case 136 further includes an upper surface 125 with an opening 126 to receive the spool 134 such that the anchor back 145 extends through the outer case 136. The opening 126 is configured to permit the spool 134 to freely rotate about the axis AAA with respect to the outer case 136. The outer case 136 also includes an inner surface 128 having dedicated slots 127 that are configured to mate with the locking clips 137 of the abutment 132 and attach the abutment to the outer case 136 and hold the spool 134 within. The inner surface 128 having a plurality of teeth 129 disposed around the inner surface 128 and engage the wings 146 of the spool 134. The outer surface of the outer case 136 further includes one or more dedicated slots 131 sized and shaped to engage a portion of the tool to hold the outer case 136 as the spool 134 is rotated with respect to the outer case 136. In the embodiment shown in FIG. 8, the outer case 136 includes three dedicates slots 131, which are equally spaced about a circumference of the outer case 136.

When assembled, the abutment 132 and outer case 136 form the components of the abutment portion 113. The outer case 136 when attached to the abutment 132 does not rotate with respect to the abutment 132. The spool 134 forms the tether portion 130. The component of the tether portion 130 rotates with respect to the components of the abutment portion 113. As shown, the component of the tether portion 130 do not move axially with respect to the components of the abutment portion 113.

The active anchor 112 includes a locked configuration and an unlocked (i.e., released) configuration. In the locked configuration, the components of the abutment portion 113 do not rotate with respect to the component of the tether portion 130. In the unlocked configuration the component of the tether portion 130 rotate about the axis AAA with respect to the components of the abutment portion 113. The locked configuration is a default configuration for the active anchor 112. A selected torque applied to the tether portion 130 with respect to the components of the abutment portion 113, such as with the tool 18, imparts the unlocked configuration. As shown, the spool 134 yieldably engages the outer case 136 such that under typical conditions the spool 134 does not rotate with respect to the abutment 132 and outer case 136. For example, the wings 146 of the spool 134 are deflectable under a selected threshold torque and yieldably urged against the teeth 129 of the outer case 136 to form an interference fit or engage with the inner surface 128. The spool 134 is configured to receive a torque with respect to the components of the abutment portion 113, such as from the tool 18. Unless the spool 134 is subjected to a torque above the selected threshold torque, the wings 146 engaged against the teeth 129 will prevent the spool 134 from rotating with respect to the components of the abutment portion 113.

If the torque applied from the tool 18 on the spool 134 surpasses the threshold, the wings 146 will deflect and are no longer pressed against the inner surface 128 or teeth 129 of the outer case 136. Accordingly, the spool 134 can rotate about the axis AAA with respect to the components of the abutment portion 13. In various embodiments of the active anchor 112, the threshold torque is only necessary to permit rotation. The tool 18 or active anchor 112 does not apply a threshold axial force to unlock the rotation, and the surgeon does not separately disengage another lock mechanism, such as a locking pin, to effect rotation. Once the torque that surpasses the threshold torque is removed, the active anchor 112 automatically transitions to the locked configuration again with the wings 146 urged against the inner surface 128 or teeth 129 of the outer case 136 to prevent the spool 134 from rotating with respect to the abutment portion 113.

Within the active anchor 112, the tether 16 can be wound around the spool 134 or, more specifically, around the winding shaft 142, to store the proximal portion of the tether 16 when the active anchor 112 is used with assembly 10. The tether 16 is configured to be threaded through the minor aperture 138 through the off-axis opening 140 and affixed to the spool 134 similar to that described above (such as tied through a hole on first surface 141). When the active anchor 112 is in the unlocked configuration of assembly 10, and the spool 134 rotated in the first direction with respect to the abutment components 113, the first length of the working portion 32 of the tether 16 is shortened, or the septal anchor 22 and the active anchor 112 are pulled toward each other, and the second length of the proximal portion of the tether 16 is lengthened as the spool 134, and in particular the winding shaft 142 of the spool 134, takes up more of the tether 16. When the active anchor 112 is in the unlocked configuration of assembly 10, and the spool 134 is rotated in the second direction opposite the first direction, the first length of the working portion 32 of the tether 16 is lengthened, or the septal anchor 22 and active anchor 112 move away from each other, and the second length of the proximal portion of the tether 16 is reduced as the spool 134, and in particular the winding shaft 142 of the spool 134, gives up more of the tether 16. When the active anchor 112 is in the locked configuration, the first length of the working portion 32 of the tether 16 and the second length of the proximal portion of the tether 16 do not change and are held in place.

Figure 9B:
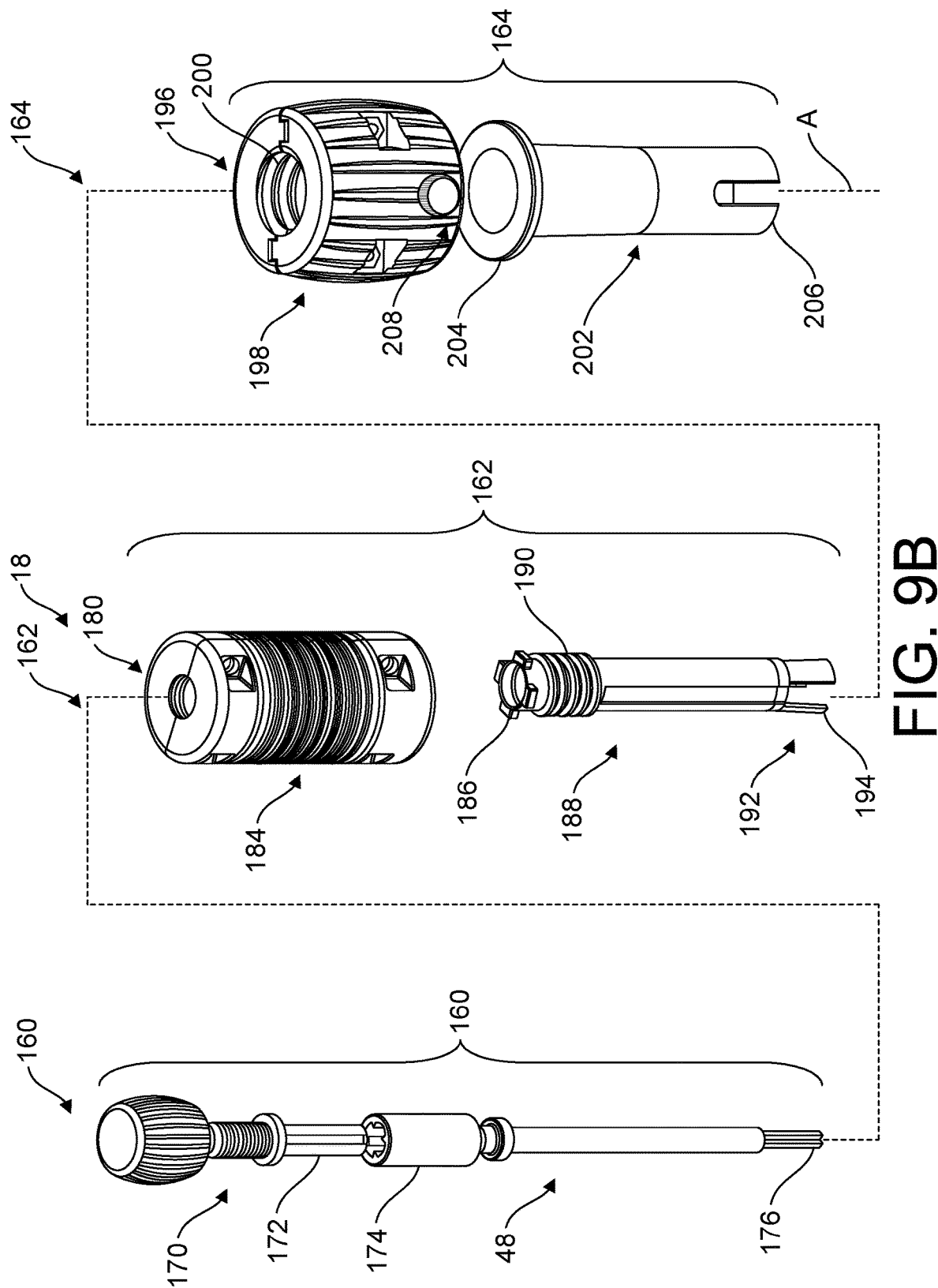
FIG. 9B is an exploded view of the example tool of FIG. 8.

FIGS. 9A and 9B illustrates an example tool 18 configured to deliver and actuate the implantable assembly 10, such as the assembly with active anchor 12 or active anchor 112. For instance, example tool 18 is described with relation to anchor 12 of assembly 10 for illustration, and other active anchors, such as active anchor 112, are compatible. In various embodiments, the tool 18 is adapted to deliver the active anchor 12 to an outer surface of the heart 5 by way of a surgical approach. In various embodiment, the tool 18 is adapted to deliver the active anchor 12 to an outer surface of the heart 5 by way of any number of known minimally-invasive surgical approaches, including for example a transthoracic or mini-thoracotomy procedure. In certain embodiments, the tool 18 is adapted to deliver the active anchor 12 to an outer surface of the heart 5 by way of a percutaneous or transvascular approach.

FIG. 9A illustrates the tool 18 includes proximal portion 2 and distal portion 3 opposite the proximal portion 2 along axis A. The distal portion 3 includes an engagement interface 150 having the adjustment key 48 configured to mate with and manipulate the anchor back 102 of the spool 60 and a grasper 152 to releasably grasp the outer case 62 of the active anchor 12. The tool 18 of the system 1 is adapted to be detachably connectable active anchor 12 via the engagement interface 150 such as to deliver the active anchor 12 through the body to the wall 4 of the heart 5. The adjustment key 48 is adapted to cooperate with the grasper 152 to apply a torque to the spool 60 (or the tether portion) with respect to the outer case 62, (of the abutment portion) so as to impart relative rotation between the two portions of the active anchor.

Operation of the adjustment key 48 with respect to the grasper 152 can adjust the tensional state of the tether 16 by means of the operation of the spool 60 in either rotational direction about the axis A. The adjustment key 48 can have a distal head with a geometry such as a polygonal geometry adapted to engage anchor back 102 to perform the adjustment of the tensional state of the tether 16. Once the operational tensional state is applied, the grasper 152 is disengaged from the outer case 62, the active anchor 12 is released from the tool 18, and the tool 18 can be removed from the body with the implanted assembly 10 in place. If an adjustment is to be made to the assembly 10, the tool 18 can be manipulated into position such that the engagement interface 150 engages or reengages the active anchor 12 such that the grasper 152 grasps the outer case 62 and the adjustment key 48 mates with the anchor back 102. The tool 18 can be applied to adjust or readjust the tensional state of the tether 16. FIG. 9B illustrates example components of the tool 18 illustrated in FIG. 9A. The tool 18 includes a locker 160 axially disposed within a holder 162, which is axially disposed within a releaser 164.

The locker 160 includes a manipulable interface 170 axially coupled via a shaft 172 to an adjuster 174. The adjuster 174 is coupled to an axial adjustment key 48 having a distal head 176 configured to mate with, such as fit around or within a structure on the anchor back 102 of the active anchor 12. In the example, the components of the locker 160, i.e., the interface 170, shaft 172, adjuster 174, and adjustment key 48 can be configured to rotate about the axis A together and not relative to each other.

The holder 162 includes an axially-extending bore 180 to coaxially receive the locker 160. The locker 160 can be configured to freely rotate about the axis A within and with respect to the holder 162 from within the bore 180. The holder 162 can be attached to the locker 160 to prevent the locker 160 from moving axially within the bore 180. The holder 162 includes a handle 184 attached to proximal end 186 of a hollow shaft 188. The hollow shaft 188 includes an outer axial thread 190 near the proximal end 186. In the illustrated embodiment, a plurality of radially-spaced fingers 192 are configured to be angled radially outwardly towards a distal end 194 of the hollow shaft 188 such that an outer diameter of the hollow shaft 188 at the proximal end 186 is less than an outer diameter of the hollow shaft 188 at the distal end 194. In another embodiment, the fingers can be straight and configured to bend, such as to bend when fitted onto the active anchor 12. In various embodiments, the distal portion of the hollow shaft 188 includes three fingers 192, which are spaced at equal distances about a circumference of the hollow shaft.

The releaser 164 includes an axially-ending bore 196 to coaxially receive the holder 162. The releaser 164 includes an interface 198 having an inner axial thread 200 configured to mate with the outer axial thread 190 of the holder 162. The releaser 164 includes an outer case configured as a hollow cylindrical shaft 202 having a proximal end 204 and a distal end 206. The proximal end 204 of the hollow cylindrical shaft 202 is coupled to the interface 198 to form the bore 196 to receive the holder 162.

In the example, the cylindrical shaft 202 includes an inner diameter that is greater than the outer diameter of the hollow shaft 188 at the proximal end 186 of the holder 162 but less than the outer diameter of the hollow shaft 188 at the distal end 194. Accordingly, as the distal end 206 of the cylindrical shaft 202 of the releaser 164 is positioned axially toward the distal end 194 of the hollow shaft 188 of the holder 162, the fingers 192 are urged radially toward the axis A. As the distal end 206 of the cylindrical shaft 202 of the releaser 164 is positioned axially toward the proximal end 186 of the hollow shaft 188 of the holder 162, the fingers 192 become more exposed from underneath the cylindrical shaft 202 and are urged radially away from the axis A. The tool 18 is configured to permit the locker 160 to freely rotate within the holder 162 even when the cylindrical shaft 202 is disposed over the fingers 192.

The releaser 164 can rotate axially relative to the locker 160 via the inner axial thread 200 in combination with the outer axial thread 190 of the hollow shaft 188, which also effects movement about the axis A. For example, a user can grip the handle 184 of the holder 162 and rotate the interface 198 of the releaser 164 with respect to the holder 162 in a first direction to axially move the distal end 206 of the cylindrical shaft 202 toward the distal end 194 of the hollow shaft 188 to cover the fingers 192 and urge the fingers 192 radially toward each other. The user can grip the handle 184 of the holder 162 and rotate the interface 198 of the releaser 164 with respect to the holder 162 in a second, opposite direction to axially move the distal end 206 of the cylindrical shaft 202 proximal from the distal end 194 of the hollow shaft 188 to uncover the fingers 192 and allow the fingers 192 to spread away from each other. A security pin 208 can be included to extend through the releaser 164 and releasably engage the holder 162 to prevent the releaser 164 from moving axially to expose the fingers 192 unless the security pin 208 is disengaged.

Figure 10A:
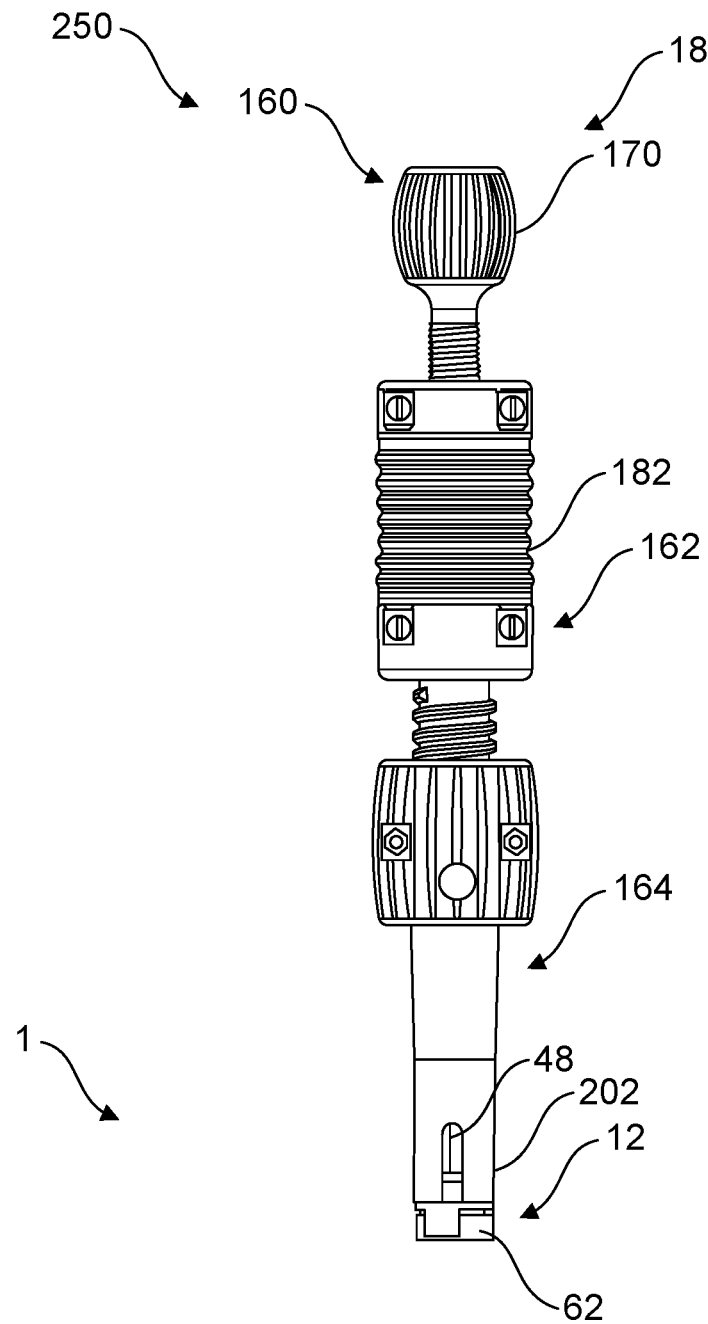
FIG. 10A is a side view of the example tool of FIG. 8 in combination with the active anchor of FIG. 5A in a coupling configuration.
Figure 10B:
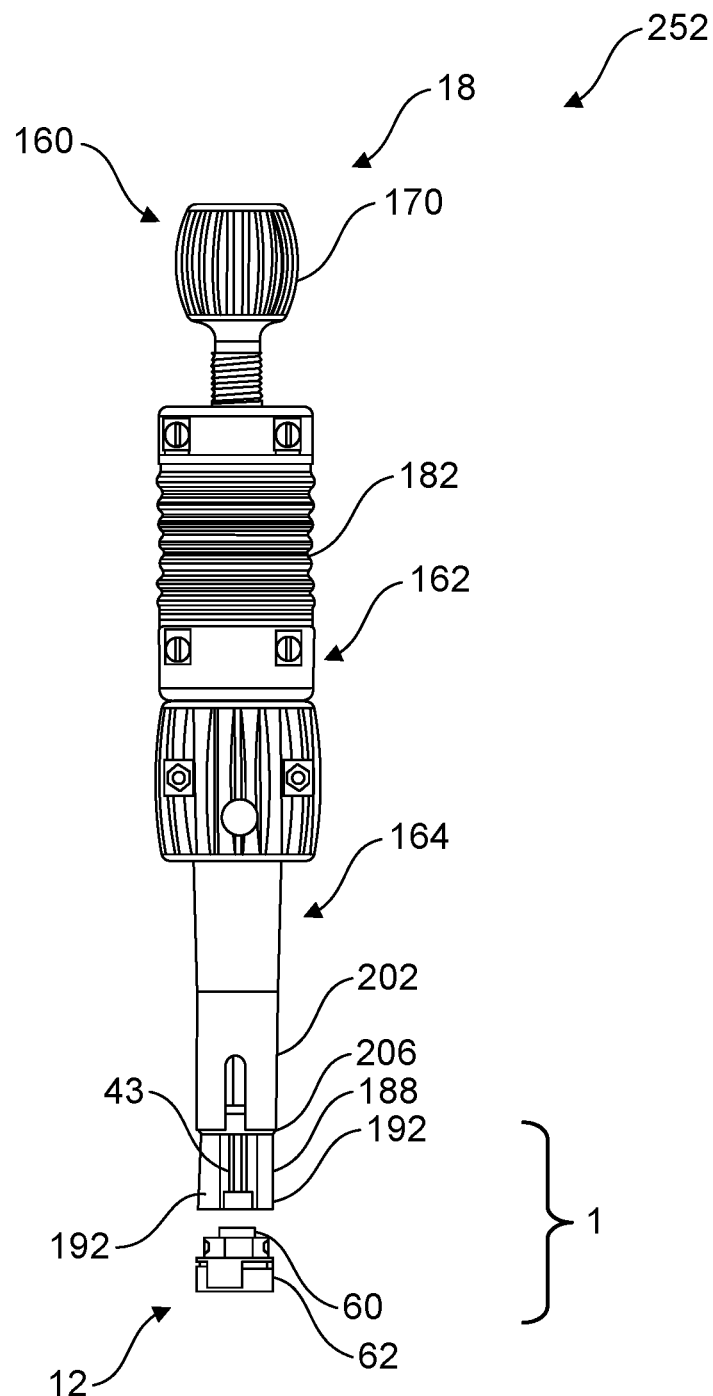
FIG. 10B is a side view of the example tool of FIG. 8 in combination with the active anchor of FIG. 5A in a decoupling configuration.

FIGS. 10A and 10B illustrate the active anchor 12 in combination with the tool 18 to form system 1. The cylindrical shaft 202 is axially movable from a coupling configuration 250, as illustrated in FIG. 10A, in which the tool 18 can be coupled to the active anchor 12 to a decoupling configuration 252, as illustrated in FIG. 10B, in which the tool 18 can be decoupled from the active anchor 12. When in the coupled configuration 250 as illustrated in FIG. 10A, the fingers 192 grasp the outer case 62 of the active anchor 12, and the fingers 192 are held in place from radially spreading apart by the cylindrical shaft 202. The distal head 176 of the key 48 is disposed to mate with the anchor back 102 of the active anchor 12. The fingers 192 within the cylindrical shaft 202 of the tool 18 can be configured to grasp the active anchor 12 with such a force as to permit the tool 18 to travel to the implantation site without the likelihood of the active anchor 12 become detached from the hold of the fingers 192. Once at the implantation site, a user can grip the handle 184 of the holder 162 and rotate the manipulatable interface 170 with respect to the holder 162 to rotate the spool 60 of the active anchor 12 via the key 48 with respect to the outer case 62 of the active anchor 12, which can adjust the tension on the tether 16. When in the decoupled configuration 252 as illustrated in FIG. 10B, the distal end 206 of the cylindrical shaft 202 is positioned proximally from the distal end 194 of the hollow shaft 188 and fingers 192 free to spread apart to release the active anchor 12. The tool 18 is decoupled from the active anchor 12.

Figure 11B:
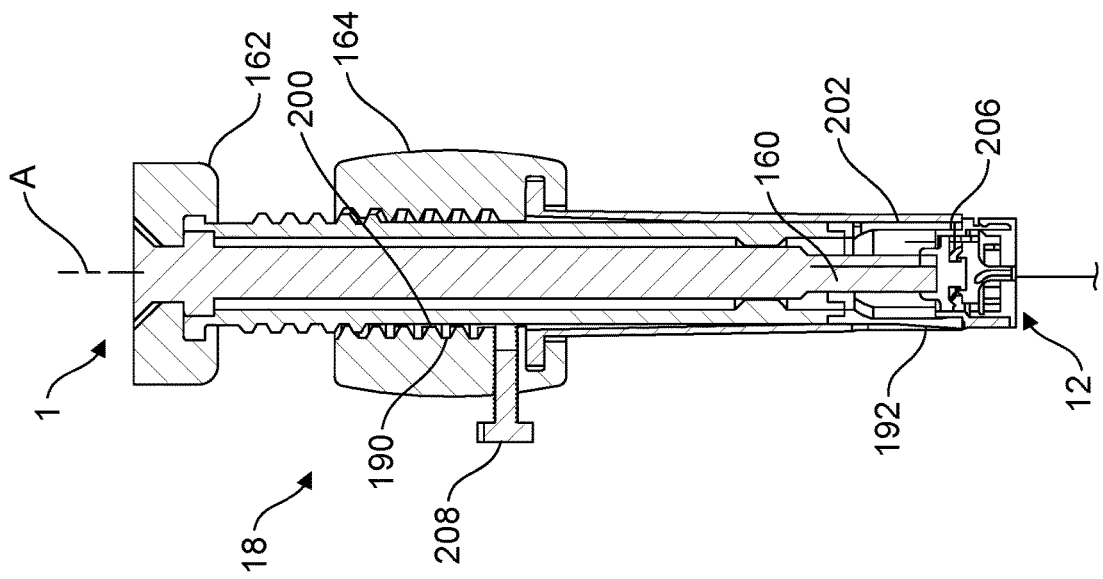
FIGS. 11A-11D are side sectioned views of the tool of FIG. 9A in combination with the active anchor of FIG. 5A illustrating an example method of transforming between the coupling configuration of FIG. 10A and the decoupling configuration of FIG. 10B.
Figure 11A:
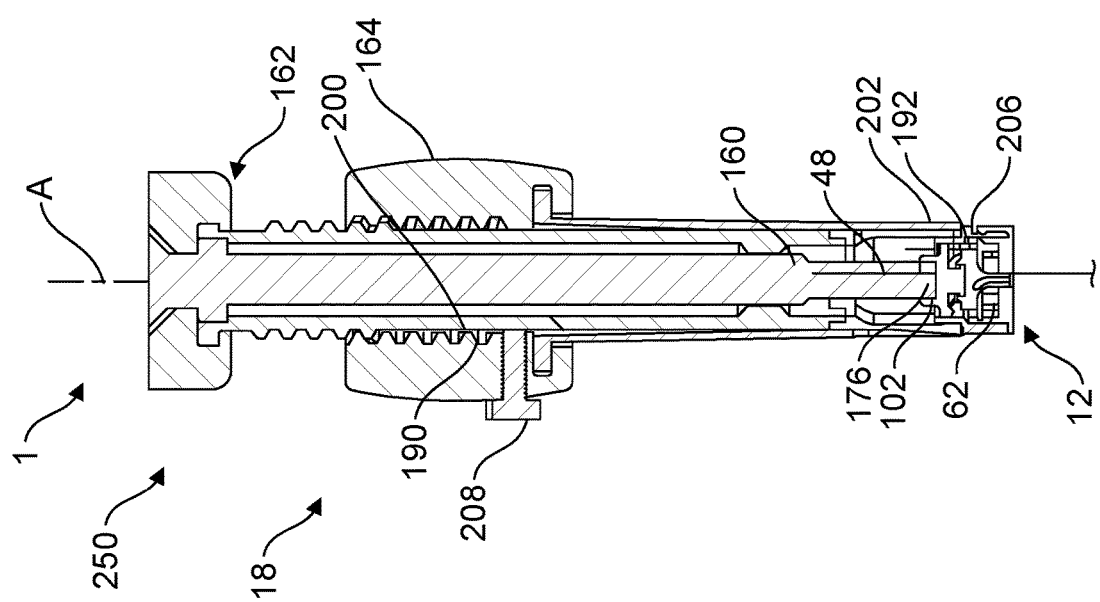
Figure 11D:
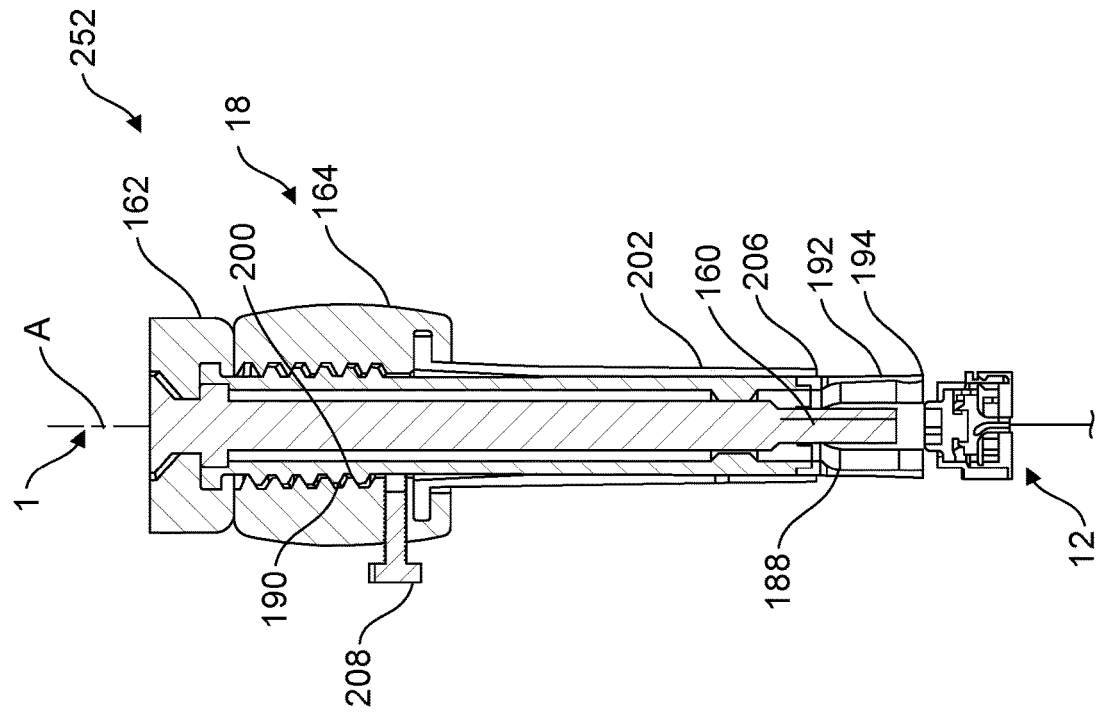
Figure 11C:
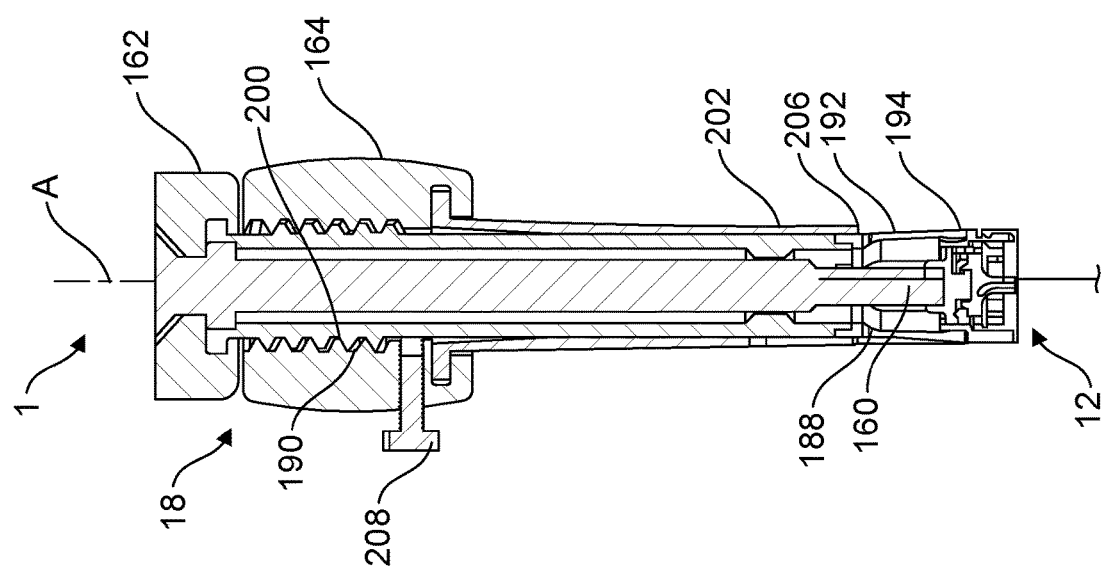

FIGS. 11A-11D illustrate the method to configure the system 1 between the coupling configuration 250 and the decoupling configuration 252. FIG. 11A illustrates the coupling configuration 250 in which the fingers 192 grasp the outer case 62 of the active anchor 12, and the fingers 192 are held in place from radially spreading apart by the cylindrical shaft 202. The distal head 176 of the key 48 is disposed to mate with the anchor back 102 of the active anchor 12. The security pin 208 is engaged and in contact with the outer axial thread 190 with the hollow shaft 188 of the holder 162 to prevent the releaser 164 from moving proximally along the axis relative to the holder 162. In the example, the engaged security pin 208 impedes the ability of the threads 190, 200 from rotating with respect to each other. FIG. 11B illustrates the security pin 208 disengaged from the holder 164 such that the outer thread 190 and inner thread 200 can rotate relative to each other. FIG. 11C illustrates that the inner axial threads 200 of the releaser 164 have been fully rotated about the outer axial threads 190 of the holder 162 to axially move the distal end of the 206 of the cylindrical shaft 202 proximal from the distal end 194 of the hollow shaft 188 to uncover the fingers 192 and allow the fingers 192 to spread away from each other and away from the active anchor 12. FIG. 11D illustrates that once the fingers 192 are spread away from the active anchor 12, the tool 18 can be decoupled from the active anchor 12.

Conversely, the tool 18 can be coupled to the active anchor 12 such as to adjust the tension of the tether 16 on a previously implanted assembly 10. The spread-apart fingers 192 can be placed around the outer case 62 of the active anchor 12 and the distal head 176 of the key 48 is disposed to mate with the anchor back 102 of the active anchor 12. The inner axial threads 200 of the releaser 164 can be rotated in an opposite direction about the outer axial threads 190 of the holder 162 to axially move the distal end of the 206 of the cylindrical shaft 202 toward from the distal end 194 of the hollow shaft 188 to cover the fingers 192 and allow the fingers 192 to grasp the outer case 62 of the active anchor 12. The security pin 208 configured to contact the hollow shaft 188 to prevent the releaser 164 from moving proximally along the axis relative to the holder 162. In various embodiments, the fingers 192 are sized and shaped to mate with the corresponding slots 131 on the outer case 136 (see, for example, FIG. 8).

The locker 160, which is now engaged with the spool 60 via the key 48, is free to rotate about the axis A with respect to the fingers 192, which are now engaged with the outer case 62 of the active anchor 12. For example, the manipulatable interface 170 can be rotated in a first direction and impart a torque greater than the threshold torque in the first direction to cause the spool 60 of the active anchor 12 to wind the tether 16 and increase the tension between the anchors 12, 22. Also, the manipulatable interface 170 can be rotated in a second direction and impart a torque greater than the threshold torque in the second direction to cause the spool 60 of the active anchor 12 to unwind the tether 16 and decrease tension between the anchors 12, 22 under traction.

FIGS. 12A-12C illustrate example positions of the manipulatable interface 170 with respect to the handle 184 of the holder 162 to configure the locker 160 to rotate in either a first direction or a second direction. For instance, as shown in FIG. 12A, the manipulatable interface 170 is configured in a first position 260 axially, with a relatively longer axial spacing between the manipulatable interface 170 and the handle 184 than in the second position. In the first position 260, the shaft 172 of the locker 160 is configured to permit the manipulatable interface 170 to rotate the distal head 176 of the locker 160 in only a first direction with respect to the fingers 192 of the holder 162, such as to wind the tether 16 on the spool 60 of the active anchor 12.

As shown in FIG. 12B, the manipulatable interface 170 is configured in a second position 262 axially, with a relatively shorter axial spacing between the manipulatable interface 170 and the handle 184 than in the first position 260. In the second position 262, the shaft 172 of the locker 160 is configured to permit the manipulatable interface 170 to rotate the distal head 176 of the locker 160 in only a second, opposite direction with respect to the fingers 192 of the holder 162, such as to unwind the tether 16 on the spool 60 of the active anchor 12.

As shown in FIG. 12C, the manipulatable interface 170 is configured in a third position 264 axially, with a relatively intermediate axial spacing between the manipulatable interface 170 and the handle 184 than in the first position 260 and second position 262. In the third position 264, the shaft 172 of the locker 160 is configured to permit the manipulatable interface 170 to rotate the distal head 176 of the locker 160 in both the first direction and the second, opposite direction with respect to the fingers 192 of the holder 162, such as to either wind or unwind the tether 16 on the spool 60 of the active anchor 12. In some embodiments, the movement of the manipulatable interface 170 axially with respect to the adjuster 174 can configure mechanisms such as limits within the adjuster 174, to lock or unlock the direction of rotation of the distal head 176 with respect to the fingers 192. In some embodiments, the shaft 172 can be slid axially within the adjuster 174 to couple with mechanisms or devices within the adjuster 174 to select positions 260, 262, 264 that lock and unlock the direction of rotation of the distal head 176 with respect to the fingers 192. Thus, the positions 260, 262, 264 can permit a user to select a direction of rotation for adjustment to reduce the likelihood for errors.

In one example, the tool 18 can include a dial with an arrow movable with respect to a graduated scale to display an amount of rotation, or rotation as an indicator of the degree of winding applied to the tether 16. For example, one of the arrow and the graduated scale can be printed on the locker 160 and the other of the graduated scale and the arrow can be printed on the holder, such as on the handle 180 and manipulable interface 170. Other configurations of the dial and arrow are contemplated, as below.

FIGS. 13A and 13B illustrate another example tool 318 configured to deliver and actuate the implantable assembly 10, such as the assembly with active anchor 12 or active anchor 112. For instance, example tool 318 is described with relation to anchor 12 of assembly 10 for illustration, and other active anchors, such as active anchor 112, are compatible. FIG. 13A illustrates the tool 318 includes proximal portion 322 and distal portion 323 opposite the proximal portion 322 along axis A. The distal portion 323 includes an engagement interface 350 having the adjustment key 348 configured to mate with and manipulate the anchor back 102 of the spool 60 and a grasper 352 to releasably grasp the outer case 62 of the active anchor 12. The tool 318 is adapted to be detachably connectable to the active anchor 12 via the engagement interface 350 such as to deliver the active anchor 12 through the body to the wall 4 of the heart 5. The adjustment key 348 is adapted to cooperate with the grasper 352 to apply a torque to the spool 60 (or tether portion) with respect to the outer case 62 (or abutment portion). Operation of the adjustment key 348 with respect to the grasper 352 can adjust the tensional state of the tether 16 by means of the operation of the spool 60 in either rotational direction about the axis A. The adjustment key 348 can have a distal head with a geometry adapted to engage anchor back 102 to perform the adjustment of the tensional state of the tether 16. Once the operational tensional state of tether 16 is adjusted, the grasper 352 is disengaged from the outer case 62, the active anchor 12 is released from the tool 318, and the tool 318 can be removed from the body with the implanted assembly 10 in place. If an adjustment is to be made to the implanted assembly 10, the tool 318 can be manipulated into position such that the engagement interface 350 engages or reengages the active anchor 12 such that the grasper 352 grasps the outer case 62 and the adjustment key 348 mates with the anchor back 102. The tool 318 can be applied to adjust or readjust the tensional state of the tether 16.

FIG. 13B illustrates example components of the tool 318 illustrated in FIG. 13A. The tool 318 includes a locker 360 axially disposed within a holder 362, which is axially disposed within a releaser 364 in a manner like tool 18 of FIGS. 9A-9B.

The locker 360 includes a manipulable interface 370 axially coupled via a threaded shaft 372 to an adjuster 374. In one embodiment, the locker 360 is a single component, and in another embodiment, the locker 360 is an assembly of two or more components. The adjuster 374 is coupled to an axial adjustment key 348 having a distal head 376 configured to mate with, such as fit around or within a structure on the anchor back 102 of the active anchor 12. The threaded shaft 372 is coupled to an indicator marker 378 that can rotate with respect to the shaft 372, and in doing so, can move axially up or down the shaft depending on the direction of rotation. In the example, the components of the locker 360, i.e., the interface 370, shaft 372, adjuster 374, and adjustment key 348 can be configured to rotate about the axis A together and not relative to each other. The indicator marker 378 can rotate with respect to the components of the locker 360 and translate axially within a range on the shaft 372.

The holder 362 includes an axially-extending bore 380 to coaxially receive the locker 360. The locker 360 can be configured to freely rotate about the axis A within and with respect to the holder 362 from within the bore 380. The holder 362 can be attached to the locker 360 to prevent the locker 360 from moving axially within the bore 380. The holder 362 includes a handle 384 attached to proximal end 386 of a hollow shaft 388. The hollow shaft 388 includes an engagement interface 350 configured as a plurality of fingers 392, which are spaced about a circumference of the hollow shaft 388. In the illustrated embodiment, the fingers 392 are configured to be angled radially outwardly towards a distal end 394 of the hollow shaft 388 such that an outer diameter of the hollow shaft 388 at the proximal end 386 is less than an outer diameter of the hollow shaft 388 at the distal end 394. In another embodiment, the fingers can be straight and configured to bend, such as to bend when fitted onto the active anchor 12.

The holder 362 also includes an indicator scale 390 that can include an axial opening 391. The indicator marker 378 of the locker 360 can fit through the opening 391 and be visible on the tool 318. For example, as the locker 360 rotates with respect to the holder 362, the indicator marker 378 moves axially up and down within the opening 391 and with respect to the indicator scale 390. The indicator scale 390 can be provided with indicia to display an amount of rotation from a starting point. For example, the indicator marker 378 can be set to the one end of the opening at the beginning of a procedure, and as the locker 360 is rotated with respect to the holder 362 in a first direction, the indicator marker 378 moves toward the other end. In one embodiment, the indicator marker 378 will move the entire length of the indicator scale 390 in a full rotation. In another embodiment, the indicator marker 378 will move the entire length of the indicator scale 390 in multiple full rotations. In one example, the indicator marker 378 set at the top of the opening 391 prevents winding in a counterclockwise direction. In another example, the indicator marker 378 set at the bottom of the opening 391 prevents winding in a clockwise direction. The indicator marker 378 is movable with respect to the graduated indicator scale 390 to display an amount of rotation in a selected direction, or rotation as an indicator of approximation or disapproximation, applied to the tether 16, or relative distance between two anchors 12, 22.

The releaser 364 includes an axially-ending bore 396 to coaxially receive the holder 362. The releaser 364 includes an interface 398 having a grip 400 near a proximal end 404. The releaser 364 includes a hollow cylindrical shaft 402 coupled to the grip 400, and the cylindrical shaft 402 includes a distal end 406. In the example, the cylindrical shaft 402 includes an inner diameter that is greater than the outer diameter of the hollow shaft 388 at the proximal end 386 of the holder 362 but less than the outer diameter of the hollow shaft 388 at the distal end 394. Accordingly, as the distal end 406 of the cylindrical shaft 402 of the releaser 364 is positioned axially toward the distal end 394 of the hollow shaft 388 of the holder 362, the fingers 392 are urged radially toward the axis A to grasp the outer case 62 of the active anchor 12 and engage the active anchor 12. As the distal end 406 of the cylindrical shaft 402 of the releaser 364 is positioned axially toward the proximal end 386 of the hollow shaft 388 of the holder 362, the fingers 392 become more exposed from underneath the cylindrical shaft 402 and are urged radially away from the axis A to spread from the outer case 62 and disengage the active anchor 12. The tool 318 is configured to permit the locker 360 to freely rotate within the holder 362 even when the cylindrical shaft 402 is disposed over the fingers 392.

The releaser 364 can rotate axially relative to the locker 360 via an inner axial thread in combination with the outer axial thread of the hollow shaft 388, which also effects movement along the axis A. For example, a user can grip the handle 384 of the holder 362 and rotate the interface 398 of the releaser 364 with respect to the holder 362 in a first direction to axially move the distal end 406 of the cylindrical shaft 402 toward the distal end 394 of the hollow shaft 388 to cover the fingers 392 and urge the fingers 392 radially toward each other. The user can grip the handle 384 of the holder 362 and rotate the interface 398 of the releaser 364 with respect to the holder 362 in a second, opposite direction to axially move the distal end 406 of the cylindrical shaft 402 proximal from the distal end 394 of the hollow shaft 388 to uncover the fingers 392 and allow the fingers 392 to spread away from each other. A security slider 408 can be included on the releaser 364 and releasably engage the holder 362 to prevent the releaser 364 from rotating with respect the holder 362. The security slider 408 can be moved away from the holder 362 to allow the releaser 364 to rotate with respect to the holder 362.

FIGS. 14A-14C illustrate the releaser 364 of the tool 318 transitioning from a coupling configuration 450 to an intermediate configuration 451 to a decoupling configuration 452 for use in system 1. The cylindrical shaft 402 is axially movable from a coupling configuration 450, as illustrated in FIG. 14A, in which the tool 318 can be coupled to the active anchor to an intermediate configuration 451, as illustrated in FIG. 14B, to a decoupling configuration 452 as illustrated in FIG. 14C, in which the tool 318 can be decoupled from the active anchor. When in the coupled configuration 450 as illustrated in FIG. 14A, the fingers 392 grasp the outer case 62 of the active anchor 12, and the fingers 392 can be held in place from radially spreading apart by the cylindrical shaft 402. The distal head 376 of the key 348 is disposed to mate with the anchor back 102 of the active anchor. The fingers 392 within the cylindrical shaft 402 of the tool 318 can be configured to grasp the active anchor 12 with such a force as to permit the tool 318 to travel to the implantation site without the likelihood of the active anchor become detached from the hold of the fingers 392. Once at the implantation site, a user can grip the handle 384 of the holder 362 and rotate the manipulatable interface 370 of the locker 360 with respect to the holder 362 to rotate the spool 60 of the active anchor 12 via the key 348 with respect to the outer case 62 of the active anchor 12, which can adjust the tension on the tether 16. Once tensioning is complete, the user can retract the cylindrical shaft 402 from the distal end 394 of the hollow shaft 388 into an intermediate configuration 451 as illustrated in FIG. 14B. In the intermediate configuration 451, the fingers 392 reduce the force on the active anchor as the cylindrical shaft 402 is moved proximally with respect to the distal end 394 of the hollow shaft 388. The proximal movement of the cylindrical shaft 402 is actuated by rotating the interface 398 in a direction via the internal threads on the cylindrical shaft 402 and the interface 398. (Distal movement of the cylindrical shaft 402 is actuated by rotating the interface 398 in an opposite direction.) When in the decoupled configuration 452 as illustrated in FIG. 14C, the distal end 406 of the cylindrical shaft 402 is positioned proximally from the distal end 394 of the hollow shaft 388 and fingers 392 are free to spread apart to release the active anchor. The tool 318 is decoupled from the active anchor.

Figure 15A:
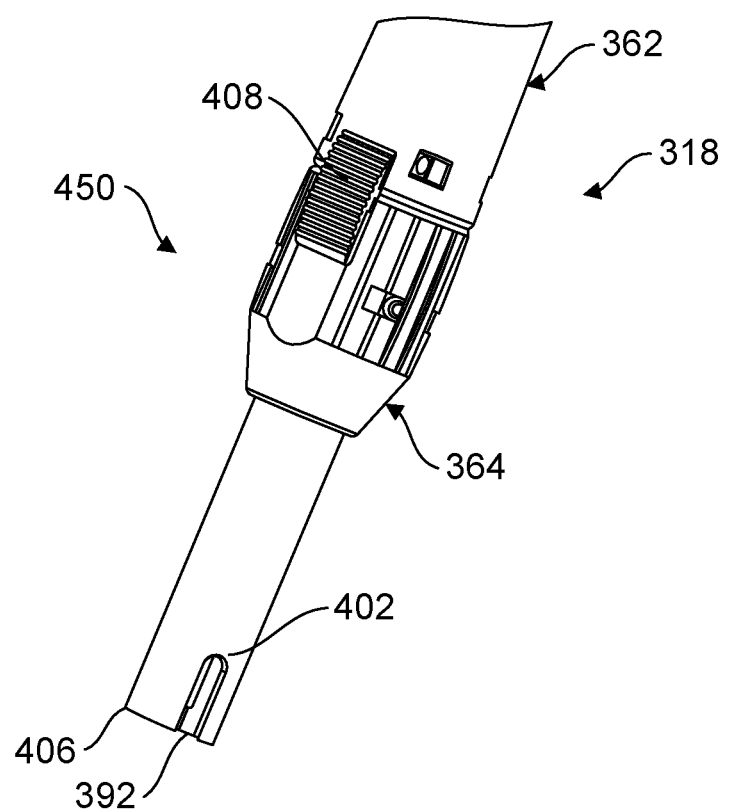
Figure 15B:
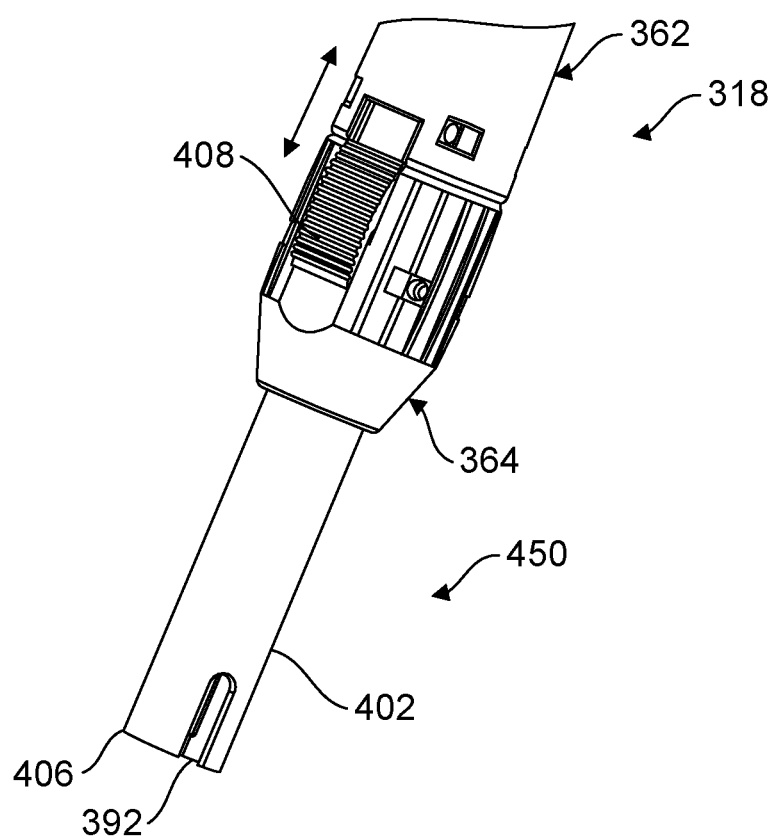
Figure 15C:
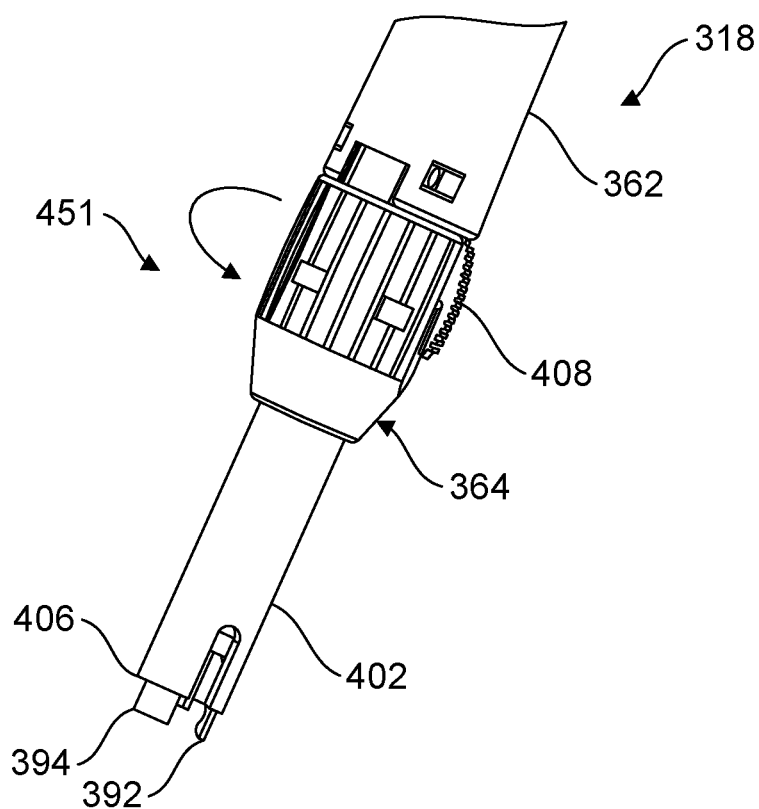
Figure 15D:
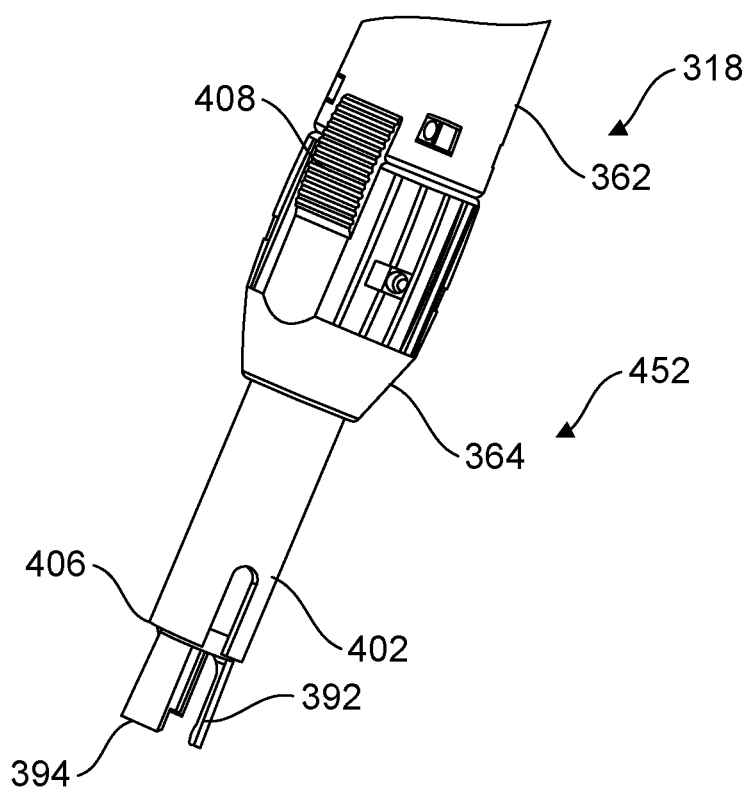

FIGS. 15A-15D illustrate the method to configure the system 1 between the coupling configuration 450 and the decoupling configuration 452. FIG. 15A illustrates the coupling configuration 450 in which the fingers 392 are configured to grasp the outer case 62 of the active anchor 12, and the fingers 392 are held in place from radially spreading apart by the cylindrical shaft 402. The distal head 376 of the key 348 is disposed to mate with the anchor back 102 of the active anchor 12. The security slider 408 is engaged and in contact with the holder 362 to prevent the releaser 364 from rotating relative to the holder 362. FIG. 15B illustrates the security slider 408 disengaged from the holder 362 such that the releaser 364 can rotate in a first direction relative to the holder 362. FIG. 15C illustrates the interface 398 of the releaser 364 being rotated with respect to the holder 362 to axially move the distal end 406 of the cylindrical shaft 402 proximal from the distal end 394 of the hollow shaft 388 into the intermediate configuration 451 and begin to uncover the fingers 392 and allow the fingers 392 to spread away from each other and away from the active anchor 12. FIG. 15D illustrates that once the fingers 392 are spread away from the active anchor, the tool 318 can be decoupled from the active anchor in the decoupling configuration 452 and the security slider 408 can be engaged and in contact with the holder 362 again to prevent rotation of the releaser 364 with respect to the holder 362. In one embodiment, the distal end 394 of the hollow shaft 388 transitions from the coupling configuration 450 to the decoupling configuration 452 in a full rotation of the releaser 364.

Conversely, the tool 318 can be coupled to the active anchor such as to adjust the tension of the tether on a previously implanted assembly. The spread-apart fingers 392 can be placed around the outer case 62 of the active anchor 12 and the distal head 376 of the key 348 is disposed to mate with the anchor back 102 of the active anchor 12. The releaser 364 can be rotated in a second direction, which is opposite the first direction, with respect to the holder 362 to axially move the distal end of the cylindrical shaft 402 toward the distal end 394 of the hollow shaft 388 to cover the fingers 392 and allow the fingers 392 to grasp the outer case 62 of the active anchor 12.

The locker 360, which is now engaged with the spool 60 via the key 348, is free to rotate about the axis A with respect to the fingers 392, which are now engaged with the outer case 62. For example, the manipulatable interface 370 can be rotated in a first direction and impart a torque greater than the threshold torque in the first direction to cause the spool 60 to wind the tether 16 and increase the tension between the active anchor 12 and the septal anchor 22. Also, the manipulatable interface 370 can be rotated in the second direction (opposite from the first direction) and impart a torque greater than the threshold torque in the second direction to cause the spool 60 to unwind the tether 16 and decrease tension between the active anchor 12 and septal anchor 22 under traction.

It is well understood that methods that include one or more steps, the order listed is not a limitation of the claim unless there are explicit or implicit statements to the contrary in the specification or claim itself. It is also well settled that the illustrated methods are just some examples of many examples disclosed, and certain steps may be added or omitted without departing from the scope of this disclosure. Such steps may include incorporating devices, systems, or methods or components thereof as well as what is well understood, routine, and conventional in the art.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An assembly adapted to be implanted by a tool, the assembly adapted for reshaping a cardiac chamber of a heart in a patient, the assembly comprising:
   an active anchor including an abutment portion adapted to abut against a wall of a ventricle of the heart and a tether portion rotatably coupled to the abutment portion, each of the abutment portion and the tether portion configured to independently couple with the tool;
   an interventricular septal anchor for coupling to a septum of the heart; and
   a tether having a working portion having a first length, extending between the active anchor and the septal anchor, and a tether proximal portion having a second length;
   wherein the abutment portion is releasably coupled to the tether portion and configured such that a predetermined torque applied to the tether portion unlocks and causes a relative rotation of the tether portion with respect to the abutment portion, which rotation adjusts the first length of the working portion and the second length of the tether proximal portion.

2. The assembly of claim 1 further comprising the tool, the tool having a tool proximal portion and a tool distal portion, wherein the tool proximal portion includes an interface and the tool distal portion includes a hollow shaft and an adjustment component adapted to engage the tether portion of the active anchor.

3. The assembly of claim 2 wherein the interface is operatively coupled to the adjustment component to allow a user to impart relative rotation to the adjustment component.

4. The assembly of claim 2 wherein a distal end of the hollow shaft includes an engagement member configured to engage the abutment portion of the active anchor so as to resist rotation thereof.

5. The assembly of claim 4 wherein the engagement member includes one or more fingers extending from the distal end of the hollow shaft.

6. The assembly of claim 1 wherein the active anchor is configured to allow the relative rotation of the tether portion with respect to the abutment portion to occur in both directions.

7. The assembly of claim 6 wherein the tether portion of the active anchor includes a winding shaft configured such that the relative rotation of the tether portion with respect to the abutment portion in a first direction causes the tether proximal portion to wind around the winding shaft and the relative rotation of the tether portion with respect to the abutment portion in an opposite direction causes the tether to unwind from the shaft.

8. The assembly of claim 1 wherein the active anchor further comprises a lock mechanism for resisting the relative rotation of the tether portion with respect to the abutment portion.

9. A system adapted for reshaping a cardiac chamber of a heart in a patient, the system comprising:
   a tool including a hollow shaft disposed about an adjustment component, the tool including an adjustment interface having a first position to allow rotation of the adjustment component in a first direction and a second position to allow rotation of the adjustment component in a second direction;
   an active anchor including an abutment portion adapted to abut against a wall of the ventricle of the heart and a tether portion coupled to the abutment portion, the tether portion configured to couple with the adjustment component of the tool;
   an interventricular septal anchor for coupling to a septum of the heart; and
   a tether having a working portion having a first length, extending between the active anchor and the septal anchor, and a tether proximal portion having a second length; and
   wherein the adjustment component of the tool is adapted to impart a torque on the active anchor so as to cause a relative rotation of the tether portion with respect to the abutment portion, which rotation adjusts the first length of the working portion and the second length of the tether proximal portion.

10. The system of claim 9 wherein the adjustment interface further has a third position to allow rotation of the adjustment component in both directions.

11. The system of claim 9 wherein the adjustment interface of the tool includes a graduated scale adapted to visually indicate a position of the adjustment component.

12. The system of claim 9 wherein the active anchor further comprises a lock mechanism for resisting the relative rotation of the tether portion with respect to the abutment portion.

* * * * *